(12) United States Patent
Lane

(10) Patent No.: US 6,623,966 B1
(45) Date of Patent: *Sep. 23, 2003

(54) NUCLEAR TARGETED PEPTIDE NUCLEIC ACID OLIGOMER

(75) Inventor: Kirk B. Lane, Brentwood, TN (US)

(73) Assignee: Vanderbilt University, Nashville, TN (US)

(*) Notice: Subject to any disclaimer, the term of this patent is extended or adjusted under 35 U.S.C. 154(b) by 122 days.

This patent is subject to a terminal disclaimer.

(21) Appl. No.: 09/935,032

(22) Filed: Aug. 22, 2001

Related U.S. Application Data

(63) Continuation of application No. 09/411,706, filed on Oct. 1, 1999, now Pat. No. 6,312,956.

(51) Int. Cl.[7] .................. C07H 21/00; C12N 15/63
(52) U.S. Cl. .................. 435/455; 514/44; 536/23.1; 536/24.5
(58) Field of Search .................. 435/455, 458, 435/461; 536/23.1, 24.3, 24.5; 514/44

(56) References Cited

U.S. PATENT DOCUMENTS

| | | |
|---|---|---|
| 5,539,082 A | 7/1996 | Nielsen |
| 5,539,083 A | 7/1996 | Cook |
| 5,656,461 A | 8/1997 | Demers |
| 5,700,922 A | 12/1997 | Cook |
| 5,705,333 A | 1/1998 | Shah |
| 5,714,331 A | 2/1998 | Buchardt |
| 5,719,262 A | 2/1998 | Buchardt |
| 5,734,034 A | 3/1998 | Jayasena |
| 5,766,855 A | 6/1998 | Buchardt |
| 5,807,746 A | 9/1998 | Lin et al. |
| 5,827,705 A | 10/1998 | Dean |
| 5,831,014 A | 11/1998 | Cook |
| 5,877,282 A | 3/1999 | Nadler et al. |
| 6,025,140 A | 2/2000 | Langel et al. |
| 6,165,720 A | 12/2000 | Felgner et al. |

FOREIGN PATENT DOCUMENTS

| | | |
|---|---|---|
| WO | 95/34647 | 12/1995 |
| WO | 96/40709 | 12/1996 |
| WO | 97/12995 | 4/1997 |
| WO | 99/13719 | 3/1999 |
| WO | 00/15824 | 3/2000 |

OTHER PUBLICATIONS

Zanta, et al., *Gene delivery: A single nuclear localization signal peptide is sufficient to carry DNA to the cell nucleus*, Proc. Natl. Acad. Sci. USA (Jan. 1999) 96:91–96.

Zelphati, et al., *PNA–Dependent Gene Chemistry: Stable Coupling of Peptides and Oligonucleotides to Plasmid DNA*, BioTechniques (Feb. 2000) 28:304–316.

Mauricio Rojas, *Genetic engineering of proteins with cell membrane permeability*, Nature Biotechnology (Apr. 1998) 370.

Liam Good, *Antisense inhibition of gene expression in bacteria by PNA targeted to mRNA*, Nature biotechnology (Apr. 1998) 355.

Gan Wang, *Peptide nucleic acid (PNA) binding–mediated induction of human globin gene expression*, Nucleic Acid Reasearch (1999) 2806–2813.

Lane; Declaration Under 37 C.F.R. 1.131 in U.S. Ser. No. 09/411,706 (2001).

Branden et al., Nature Biotechnology 17 (8), 784–787 (Jul. 1999).

*Primary Examiner*—Kenneth R. Horlick
(74) *Attorney, Agent, or Firm*—Waddey & Patterson, P.C.; Douglas W. Schelling

(57) ABSTRACT

A composition comprising a nuclear localization sequence and a peptide nucleic acid oligomer (NLS-PNA) is described. Uses of the composition include, but are not limited to: regulation of gene expression, gene therapy, and the production of pharmaceutical nucleic acids and proteins. In addition, the NLS-PNA is useful for scientific and therapeutic transfection and expression of nucleic acids in cells types that previously were resistant to transfection and therapy including quiescent cells, differentiated cells, embryonic stem cells, and eukaryotic cells with intact nuclear membranes. The NLS-PNA can be combined with a membrane transport sequence (MTS) forming a novel compound referred to as an MTS-NLS-PNA wherein the MTS provides transport through the cytoplasmic membrane of a cell. A nuclear targeted peptide nucleic acid oligomer is useful for the treatment of genetic based diseases and diseases that can be treated genetically including heart disease, cancer, cerebrovascular diseases, chronic pulmonary diseases, human immunodeficiency virus, and other diseases, conditions and disorders.

15 Claims, 4 Drawing Sheets

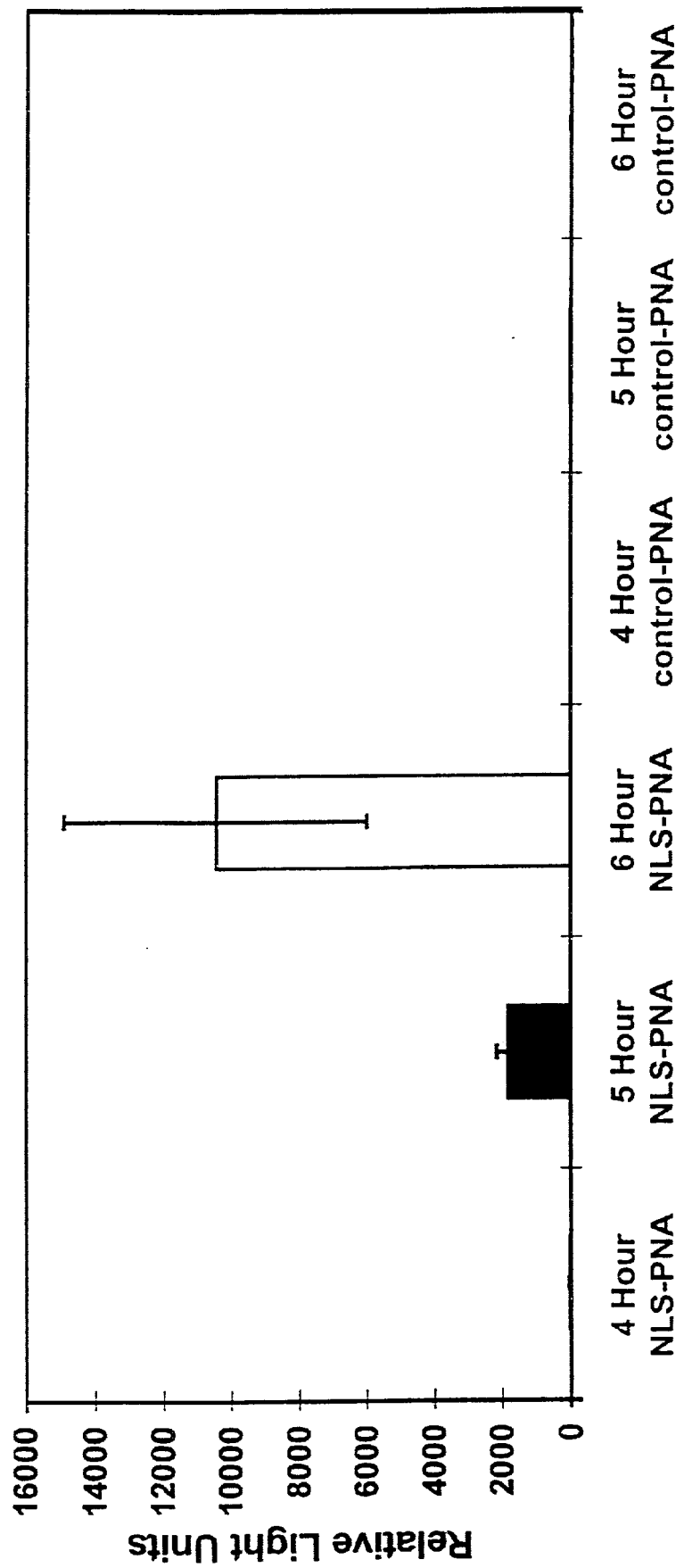

NUCLEAR TARGETED PEPTIDE NUCLEIC ACID OLIGOMER

This application is a continuation application of and claims priority to U.S. patent application Ser. No. 09/411,706, filed Oct. 1, 1999, now U.S. Pat. No. 6,312,956, entitled "Nuclear Targeted Peptide Nucleic Acid Oligomer". The contents of Ser. No. 09/411,706 are incorporated herein by reference.

The government owns rights in the present invention pursuant to grant numbers 5 T32 HL07123 and 5 RO1 HL45151 both from the National Institutes of Health.

BACKGROUND OF THE INVENTION

1. Field of the Invention

The present invention relates generally to the transfection of eukaryotic cells, the regulation of gene expression, and gene therapy. In particular, the present invention relates to novel compositions and uses thereof including, but not limited to: the regulation of nucleic acid expression, the transfection of eukaryotic cells, gene therapy, the creation of transgenic animals, the biological production of pharmaceuticals, and the treatment of a variety of human diseases and disorders.

2. Description of Related Art

The State of the Technology: Gene Transfer

One of the most utilized and important techniques employed in the biological sciences today is the transfer of foreign nucleic acids into cells in vitro and in vivo. This technology is the foundation for gene therapy. A primary obstacle to the successful implementation of gene transfer technology is that cellular membranes provide a significant barrier to the translocation of nucleic acid. Currently, techniques exist for the transfer of nucleic acids across the cytoplasmic membrane of prokaryotic (transformation) and eukaryotic cells (transfection) including chemical, physical, and biological methods such as: calcium phosphate co-precipitation, DEAE dextran treatment, electroporation, microinjection, biolistic bombardment, viral infection, and liposomal based methods. The nuclear membrane of eukaryotic cells, however, proves to be a more formidable challenge. This membrane is a barrier to the passive movement of macromolecules larger than 15,000 kDa. Empirically, transfection protocols are limited to rapidly dividing cells. The hypothesis for these observations is that transfected nucleic acids have access to the nuclear compartment only when the nuclear membrane is dissolved during mitosis. Without a nuclear membrane, the transfected nucleic acids are thought to distribute throughout the volume of the cell, and a portion of these nucleic acids might remain in the nucleus after the nuclear membrane reforms.

Various strategies have been attempted to circumvent an intact nuclear membrane during transfection. Several viral vectors are under study as gene transfer agents, but all of them have major disadvantages. Viral vectors are a biohazard, it is usually necessary to employ procedures to limit viral replication by eliminating certain viral genes and using helper virus strains, the gene of interest must be cloned into the viral vector, and adeno-associated vectors (AAV) are difficult to produce in large quantities and have a limited capacity for accepting large transgenes. The transfection efficiency of most viral vectors is dependent upon proliferation of the host cell which, again, limits the utility of such vectors. Replication deficient adenoviral vectors have been used extensively in the lungs, but trigger an acute inflammatory response and a chronic immune response. Retroviral vectors, which insert randomly into the host genome, have the potential to disrupt normal genes and carry a risk of inducing malignancies. Thus, viral vectors show limited utility for in vivo therapy.

Several non-viral strategies to circumvent an intact nuclear membrane during transfection have been investigated, but none has proven to be efficient. One attempt is described in U.S. Pat. No. 5,827,705 to Dean. The Dean U.S. Pat. No. 5,827,705 patent utilizes a nucleic acid segment, referred to as a nuclear transport sequence (NTS), found to promote the transport of plasmid DNA into the nucleus of several cell types following microinjection of the plasmid into the cell. This approach has several major drawbacks including the need to clone the gene of interest into this specialized plasmid and the need for microinjection into individual cells as part of the transfection procedure.

Another attempt was described by Rossi et al. (1993). A plasmid DNA was covalently linked to a nuclear localization sequence (NLS) for nuclear import; however, this system damages the DNA making it non-viable for expression or replication.

Still another transfection method was described in U.S. Pat. No. 5,807,746 to Lin et al. In the Lin U.S. Pat. No. 5,807,746 patent, an importation competent signal peptide (ICSP) was demonstrated to promote the passage of a biologically active peptide through the cytoplasmic membrane. The ICSP was also made in conjunction with an NLS (ICSP-NLS). The ICSP-NLS promoted the passage of the biologically active peptide into the nuclear compartment. The Lin U.S. Pat. No. 5,807,746 patent suggested methods for linking nucleic acids to the ICSP-NLS using charge association or covalent linkage by thioester bonds. However, charge-association is too weak of an interaction for efficient transfection (Fritz et al. (1996) Human Gene Therapy 7:1395–1404) and covalent linkage eliminates the functionality of the nucleic acid (Rossi et al. (1993) Molecular & General Genetics 239:345–353).

A second major challenge to the successful implementation of gene transfer technologies involves the phenomenon of gene silencing or transient expression of transferred nucleic acids. This effect is characterized by the termination of transgene expression within three or four days of transfection. One explanation for this phenomenon is that the foreign nucleic acids are transported out of the nucleus by a cellular process (Alwine (1985) Mol Cell Biol 5:1034–1042). The common redress in vitro for transient expression is to employ selection methods to kill cells that do not express a co-transfected detoxifying agent. What is needed is a system that retains viable nucleic acids and plasmids in the nucleus which are capable of long-term expression without the need for toxic selective agents.

The State of the Technology: Peptide Nucleic Acid

Peptide nucleic acids (PNAs) are analogs of nucleic acids in which the ribose-phosphate backbone has been replaced with a backbone that is held together by amide bonds as described in U.S. Pat. No. 5,539,082 to Nielsen et al. PNAs have several interesting features, including the ability to hybridize to complementary DNA, RNA, or peptide nucleic acid (PNA) sequences. The hybridization of a PNA to a complementary sequence is generally greater than that of nucleic acid to nucleic acid hybrids (Good and Nielsen (1997) Antisense and Nuc Acid Drug Dev (7)431–7). Furthermore, PNAs are resistant to proteases and nucleases, and exhibit an ability to modulate transcription in a positive direction when hybridized to the non-coding strand of a promoter region and in a negative direction when hybridized to the coding strand of a promoter region (N. E. Mollegaard (1994) Proc. Natl. Acad. Sci. 91(9)3892–3895; Good and Nielsen, 1997). Specific PNA molecules have been used as antisense oligonucleotides (Good and Nielsen (1998) Nature Biotechnology (16)355–358), transcription enhancers and transcription repressors (N. E. Mollegaard, 1994; Good and Nielsen, 1997; Wang et al. (1999) Nuc Acids Res 27:2806–2813), and PCR™ clamping reagents (U.S. Pat. No. 5,656,461 to Demers).

Deficiencies Inherent in the State of the Technology

Current transfection methods are inefficient. Particularly lacking are methods for transfecting cells with an intact nuclear membrane. Methods for transfecting mitotic cells (in which the nuclear membrane has dissolved) are also limited because only a few percent of cells in a given population are mitotic and because transgene silencing eliminates expression within a few days without selective agents and the additional transfection of selection resistance genes. Improved transfection methods would benefit both basic scientific research and clinical medicine. The limited success of gene therapy thus far can be attributed to procedures that target actively dividing cell populations and likely achieve expression in less than one percent of targeted cells. Improved transfection methods that permit the efficient transfection of nucleated cells would immediately yield dramatic improvements in basic science, clinical medicine, and especially gene therapy. Benefits would include: the ability to express a gene in a greater percentage of any population of cells (including actively dividing cell populations), the ability to transfect all cell types (including quiescent, non-dividing, differentiated, and the like), reducing the dosage of gene therapy required to achieve an effect, reducing toxicity, and enhancing opportunities for routes of administration. In addition, it would be helpful if such a system were capable of regulating expression of any endogenous or exogenous nucleic acid.

SUMMARY OF THE INVENTION

The present invention provides compositions and methods for use thereof that overcome deficiencies in the prior art related to, but not limited to: transfection of eukaryotic cells, regulation of gene expression, regulation of epigenetic gene expression, production of nucleic acid and protein pharmaceuticals, and gene therapy.

The present invention is directed to a composition comprising a nuclear localization sequence (NLS) and a peptide nucleic acid (PNA) (the combination referred to herein as an NLS-PNA) which is useful for transferring a nucleic acid into the nucleus of a cell; for regulating an expression of the transferred nucleic acid, of an endogenous nucleic acid, or an epigenic nucleic acid; for the creation of transgenic animals; and as a gene therapy agent. The NLS-PNA is also useful in conjunction with cells that were previously refractory to transfection.

In certain embodiments, the PNA is annealed to a complementary region of the nucleic acid (NA) to form a stable NLS-PNA-NA. The NLS-PNA-NA can be transfected into the cytoplasm of a nucleated cell using standard methods. The NLS transports the entire NLS-PNA-NA from the cytoplasm into the nuclear compartment and maintains the localization of the NLS-PNA-NA in the nuclear compartment. Annealing of the PNA to the nucleic acid does not damage the nucleic acid; thus, the nucleic acid is capable of expressing a gene product. The nucleic acid may include a coding strand and a non-coding strand. Annealing of the PNA to the non-coding strand, especially in the region of the promoter, stimulates expression of the gene product. In certain embodiments, an NLS-PNA can be used to transfer a nucleic acid into the nucleus of an embryonic stem cell for the creation of a transgenic animal.

An NLS-PNA can be used in any gene therapy application as a rescue agent to enhance or suppress expression of the gene therapeutic by targeting the PNA to a non-coding or a coding strand of the gene therapeutic, respectively, especially in the region of a promoter.

An NLS-PNA can also be used to regulate an expression of a nucleic acid segment, including a gene, in a nucleus of a cell. The NLS-PNA can be transfected into the cytoplasm of a nucleated cell using standard methods. The NLS transports the entire NLS-PNA from the cytoplasm into the nuclear compartment and maintains the localization of the NLS-PNA in the nuclear compartment. The PNA portion of the NLS-PNA is designed to be complementary to a region on the targeted nucleic acid segment. The PNA anneals to the complementary region and, accordingly, enhances or suppresses an expression of the nucleic acid segment. Multiple nucleic acid segments (including introns and exons of a gene or multiple genes) can be targeted at once with one NLS-PNA or with distinct NLS-PNAs. In certain embodiments, annealing of the PNA to a viral nucleic acid inhibits an activity of the viral nucleic acid or an expression of a viral gene product. It is contemplated that the nucleic acid includes, but is not limited to, single-stranded nucleic acid, double-stranded nucleic acid, DNA, RNA, and single- or double-stranded viral nucleic acid.

In certain embodiments, the NLS-PNA is introduced into the cytoplasm of the cell by combining the NLS-PNA with a membrane transport sequence (MTS). This novel composition is referred to herein as an MTS-NLS-PNA, but the elements can be combined in any order. An MTS and its use in translocating a cytoplasmic membrane are described in U.S. Pat. No. 5,807,746 to Lin et al., incorporated herein by reference.

It is an object of the present invention to provide compositions useful as transfecting reagents.

It is a further object of the present invention to provide a system designed to transfer a nucleic acid into the nucleus of a eukaryotic cell including, but not limited to: a yeast cell, an insect cell, a plant cell, an animal cell, a mammalian cell, a mouse embryonic cell, a human cell, and a hybrid cell.

It is an additional object of the present invention to provide a system designed to transfect a nucleic acid into a nucleus of a eukaryotic cell including, but not limited to: a cell with an intact nuclear membrane, a non-dividing cell, a quiescent cell, a terminally differentiated primary cell, an embryonic stem cell, and the like.

It is another object of the present invention to enhance the transfection efficiency for transfection of dividing populations of eukaryotic cells.

It is still another object of the present invention to provide a system designed to stimulate the expression of a nucleic acid transfected into a eukaryotic cell, especially without the need to utilize toxic selection agents or resistance genes.

It is yet another object of the present invention to provide a system designed to regulate an expression of a nucleic acid transfected into a nucleus of a eukaryotic cell, including the rescue (treatment) of an overabundant or an insufficient gene therapy.

It is yet a further object of the present invention to provide a system designed to regulate an expression of a nucleic acid segment, wherein the nucleic acid segment is in the nucleus of a eukaryotic cell, and wherein the regulation includes stimulation of expression or inhibition of expression. One aspect of the present object includes the prevention and treatment of a medical condition or disease through the medically relevant regulation of the nucleic acid segment. Another aspect of the present object includes kits designed for use in the prevention or treatment of a medical condition or disease through the medically relevant regulation of the nucleic acid segment.

It is also an object of the present invention to provide compositions and methods useful for in vitro transfection, in vivo transfection, ex vivo transfection, in situ labeling, diagnostic tests, genetic therapy, gene therapy, treatment of medical conditions, and the creation of transgenic animals. One aspect of the present object comprises kits designed for in vitro transfection, in vivo transfection, ex vivo transfection, in situ labeling, diagnostic tests, genetic therapy, gene therapy, treatment of medical conditions, and the creation of transgenic animals.

Accordingly, the present invention includes a composition comprising a nuclear localization sequence (NLS) and a peptide nucleic acid (PNA). The preferred method of making an NLS-PNA comprises solid phase synthesis of a single sequence of amino acids residues (for the NLS portion) and peptide nucleic acid residues (for the PNA portion), wherein the residues are linked by peptide bonds. A PNA comprises a nucleic acid analog in which nucleic acid bases are attached to a peptide backbone through a suitable linker, as described in U.S. Pat. No. 5,539,082 to Nielsen et al., incorporated herein by reference.

Accordingly, the present invention provides methods for transferring a nucleic acid into a nucleus of a cell using compositions disclosed herein. In certain embodiments, a PNA is annealed to a complementary region of a desired nucleic acid and transfected into the cytoplasm of the cell using methods known to one with skill in the art. The NLS-PNA-NA translocates from the cytoplasm into the nucleus through the action of the NLS. In other embodiments, an MTS-NLS-PNA is annealed to a region of the nucleic acid and transferred into the nuclear compartment of a cell simply by putting the MTS-NLS-PNA-NA in contact with the cell.

Accordingly, the present invention can include a nucleic acid. The nucleic acid can be single-stranded, double-stranded, DNA, RNA, an expression vector, an expression vector with an insert, a plasmid, a circular nucleic acid, a linear nucleic acid, a viral vector, a therapeutic vector, and the like. In certain embodiments, the nucleic acid comprises an antisense nucleic acid targeted to complementary sequences in the nucleus. Specifically, the bridging of introns, exons, and intron-exon boundaries is contemplated with antisense strands or antisense encoding vectors. In certain embodiments, the nucleic acid encodes an expression product, wherein the expression product comprises a peptide, a polypeptide, a protein, a fusion protein, or an antisense nucleic acid. In certain embodiments, an NLS-PNA (or an MTS-NLS-PNA as described herein) has an antisense activity, wherein the antisense activity is localized in the nucleus, not in the cytoplasm because the NLS directs the activity to the nucleus and retains it in the nucleus. U.S. Pat. No. 5,700,922 to Cook, incorporated herein by reference; describes the use of PNA-DNA-PNA chimeras in non-nuclear antisense reactions. In certain embodiments wherein an antisense nucleic acid is expressed from a nucleic acid annealed to an NLS-PNA (or an MTS-NLS-PNA as described herein), the antisense reaction can take place in any compartment of the cell or even outside of the cell. In certain embodiments, the nucleic acid encodes a gene, a reporter gene, a gene fusion, a transgene, or a therapeutic gene. A particularly useful nucleic acid, comprises a double-stranded expression vector with an insert under the control of a cytomegalovirus (CMV) promoter. The preferred PNA sequence, for use with this nucleic acid, comprises the peptide nucleic acid sequence ACTGCCCA which is complementary to a region on the non-coding strand of the CMV promoter.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4 is a graph showing the relative expression of a luciferase reporter gene (in relative light units) for transfections of contact inhibited HeLa cells with 300 ng of pCMV-Luc plasmid annealed to either CMV specific NLS-PNA or control-PNA in a 1:3 ratio (M/M) as described in Example 5. Cells were harvested at 4, 5, and 6 hours after transfection. Contact inhibited HeLa cells are known in the prior art to be refractory to transfection with exogenous nucleic acids.

Figure 1:
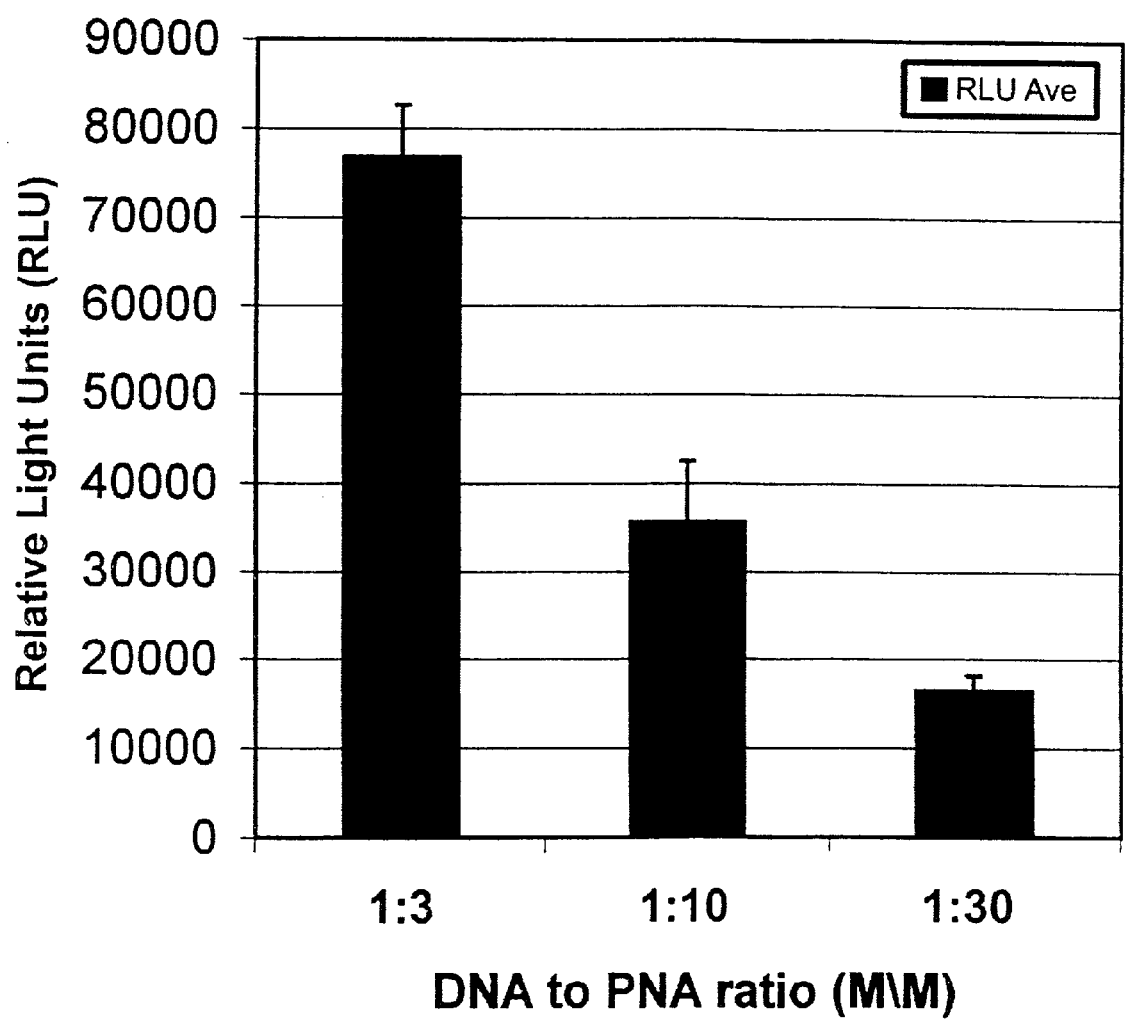
FIG. 1 is a graph showing the relative expression of a luciferase reporter gene (in relative light units) for transfections of sub-confluent HeLa cells with pCMV-Luc plasmid DNA annealed to control-PNA in ratios of 1:3, 1:10, and 1:30 (M/M) as described in Example 2. This provides a PNA dose-response curve.

DESCRIPTION OF THE PREFERRED EMBODIMENTS 1.00 Definitions

Following long standing patent law convention, the singular forms "a," "an," and "the" include plural references in this specification, including the claims, unless the content clearly dictates otherwise.

In describing the present invention, the following terms are used. The meanings of the terms are understood by one of ordinary skill in the art to generally include the information provided, unless clearly indicated otherwise. These terms are listed by way of example so that the invention may be more easily understood. The terms "amino acid", "nucleic acid", "nucleic acid sequence", "polynucleotide", and "amino acid sequence" are known to one of ordinary skill in the art. Definitions of these terms are found in the World Intellectual Property Organization (WIPO) Handbook on Industrial Property Information and Documentation, Standard ST.25: Standard for the Presentation of Nucleotide and Amino Acid Sequence Listings in Patent Applications (1998), including Tables 1 through 6 in Appendix 2, incorporated herein by reference (Hereinafter "WIPO Standard ST.25 (1998)"). In certain embodiments of the present invention, these terms include derivatives and analogues including D- and L-amino acids. The terms "amino acid", "nucleic acid", "nucleic acid sequence", and "amino acid sequence" do not refer, however, to peptide nucleic acid or derivatives thereof, as hereby specifically defined and used herein.

The term "nuclear localization sequence" or "NLS" is used to indicate a peptide, or derivative thereof, that directs the transport of a peptide, protein, or molecule associated with the NLS; from the cytoplasm into the nucleus of the cell across the nuclear membrane. Furthermore, a peptide that contains a "nuclear localization sequence" and additional amino acid sequences could be used as a "nuclear localization sequence" for the purposes of the present invention Adam et al. (1990) J. Cell. Biol. 111:807–818). In certain embodiments, an NLS may be composed of D- or L-amino acids.

The term "bipartite nuclear localization sequence" is used to indicate a type of NLS that typically has about two basic amino acids separated by a spacer of about four to about fifteen amino acids from a second cluster of usually more than about three basic amino acids. A bipartite NLS may be composed of D- or L-amino acids.

The term "membrane transport sequence" or "MTS" is used to indicate a peptide, or derivative thereof, that directs the transport of a peptide, protein, or molecule associated with the MTS; from the outside of a cell into the cytoplasm of the cell through a cytoplasmic membrane of the cell. Furthermore, a peptide that contains a "membrane transport sequence" and additional amino acid sequences could be used as a "membrane transport sequence" for the purposes of the present invention. An MTS may be composed of D- or L-amino acids.

The terms "peptide", "polypeptide", and "protein" are used interchangeably and refer to any polymer of amino acids (dipeptide or greater) linked through peptide bonds. Thus, the terms "peptide", "polypeptide", and "protein" include oligopeptides, protein fragments, analogues, nuteins, fusion proteins and the like. The terms "peptide", "polypeptide", and "protein" do not include "peptide nucleic acids" as specifically defined and used herein.

A "derivative" of a polypeptide is intended to include homologous polypeptides in which conservative amino acid substitutions have been made, as well as to include other amino acid substitutions that result in a polypeptide that retains its function, e.g., as in derivatives of an NLS or an MTS.

The terms "peptide nucleic acid", "PNA", and "PNAs" are used interchangeably and are intended to refer to a class of compounds that includes ligands such as naturally occurring or synthetic DNA bases attached to a peptide backbone through a suitable linker. The terms "PNA sequence" and "PNA oligomer" are used interchangeably herein and are intended to refer to a polymer of "PNA" subunits linked together by amide bonds. A "PNA sequence" and "PNA oligomer" includes two or more "PNA" subunits. A "PNA" sequence" and "PNA oligomer" can include additional non- "PNA" subunits. For example a "PNA sequence" or a "PNA oligomer" can include nucleotides and/or amino acids or polymeric compositions thereof (wherein nucleotides and peptides are defined in WIPO Standard ST.25 (1998)). These molecules are referred to as "PNA sequences" and "PNA oligomers" herein, given at least two peptide nucleic acid subunits linked by a peptide bond. "PNAs" can anneal to a complementary nucleic acid sequence, wherein the "PNA sequence" refers to the order of the nucleotidic sidechains which are attached to the peptide backbone. Numerous varieties of "PNAs" are described including, but not limited to: glycine based backbones, alanine based backbones, lysine based backbones, amino acid side chains, mixed "PNA and nucleic acid chains", mixed "amino acid and PNA chains", and the like. "PNAs" can be developed with any kind of amino linkage, sidechain, amino sidechain, linkage, or nucleotidic sidechain. The term "PNA" is specifically defined and used herein to not include the definitions of "nucleotide", "nucleic acid sequence", "amino acid", or "amino acid sequence". Mixed species of "PNA and nucleic acids" or "PNA and amino acids" can be referred to as "PNA nucleic acid chimeras" or "PNA amino acid chimeras", given at least two "PNA" subunits linked together by a peptide bond. A composition comprising a PNA and an NLS is specifically referred to herein as an NLS-PNA. A combination comprising a PNA, an NLS, and a nucleic acid is specifically referred to herein as an NLS-PNA-NA. A composition comprising an MTS, a PNA, and an NLS is specifically referred to herein as an MTS-NLS-PNA. A composition comprising an MTS, a PNA, an NLS, and a nucleic acid is specifically referred to herein as an MTS-NLS-PNA-NA.

A nuclear transfection complex is a term used herein to mean a composition comprising a nuclear localization sequence, a peptide nucleic acid oligomer, and a nucleic acid and is also referred to herein as an NLS-PNA-NA. In certain embodiments, the NLS and the PNA portions of the nuclear transfection complex will be combined by a peptide bond and a region of the nucleic acid with a complementary sequence to the PNA, will be annealed to the PNA portion of the nuclear transfection complex.

An expression regulator is a term used herein to mean a composition comprising a nuclear localization sequence and a peptide nucleic acid oligomer and is also referred to herein as an NLS-PNA. In certain embodiments, the PNA portion of the expression regulator will be complementary to a region of sequence on a nucleic acid which is the target for regulation.

The term "refractory cell type" is used to indicate a cell type that is resistant to being experimentally altered, especially in terms of being resistant to the transfection of an exogenous nucleic acid, and more especially in terms of being resistant to the transfection and expression of an exogenous nucleic acid. Examples in the prior art of cells that are typically resistant to transfection include, but are not limited to: non-dividing cells, quiescent cells, terminally differentiated primary cells, populations of dividing cells with fewer than 50% of cells undergoing mitosis, tumor cells, cancer cells, and embryonic stem cells.

The term "transfect", "transfection" or "transfecting" is used to indicate the act or method of introducing a molecule, usually a nucleic acid, into a cell. As used herein in certain preferred embodiments, "transfect" includes the introduction of a nucleic acid as well as other compositions of the present invention including, but not limited to, peptides and peptide nucleic acids into a cell, wherein the cell is preferably a eukaryotic cell.

Meanings of the term "gene expression" are known to those with skill in the art. "Gene expression" includes the production of a protein from RNA or DNA and production of a RNA from a DNA. A gene is said to be "expressed" when it is transcribed into RNA, but this meaning also includes translation into a peptide or protein. The term "gene expression" is often shortened to "expression", "expressed", or the like. Additional meanings of the term "gene expression" are known to those with skill in the art.

The term "consensus sequence" is used herein to indicate a sequence of general agreement between multiple nucleic acid or peptide sequences that are aligned and examined for sequence similarities. Several programs are commonly used in the scientific community to perform sequence alignments. These include BLAST for nucleotide sequence alignments and FASTA for peptide or protein alignments. In certain embodiments herein, the term "consensus sequence" refers to a window of similarity which may or may not include the entire sequence of one or more sequences under comparison.

The terms "homologous", "homology", "sequence homology" can be used interchangeably and indicate a relative degree of sequence identity between two or more biologically relevant sequences. Homology can be determined, for example, between two peptide sequences by aligning the sequences to obtain a best alignment or a preferred alignment (programs such as FASTA in the case of peptide sequences can be helpful); the number of identical amino acids in the alignment and the total number of amino acids are counted; and the homology is usually represented as a percentage (the ratio of identical units to total units, amino acids in this example, multiplied by one hundred).

The terms "treatment" and "therapy" are used interchangeable herein and refer to: the prevention of infection or reinfection (prophylaxis), the prevention of symptoms of a disease of interest, or the reduction or elimination of symptoms of a disease of interest.

Meanings of the terms used herein are known to those of ordinary skill in the art and can include meanings not specifically mentioned in the definitions above, which are provided by way of example.

2.00 Nuclear Localization Sequence (NLS)

An NLS comprises a naturally occurring peptide sequence contained in native proteins targeted for import into the nuclear compartment. Following synthesis of nuclear proteins outside of the nucleus, the NLS moves the nuclear proteins into the nuclear compartment by interacting with pores in the nuclear membrane. Proteins or molecules that contain or are associated with an NLS have been demonstrated to be transported into the nuclear compartment (e.g., see U.S. Pat. No. 5,807,746 to Lin et al., and U.S. Pat. No. 5,877,282 to Nadler et al.; each patent incorporated herein by reference). It is clear that many distinct peptide sequences can function as an NLS, but typical NLSs contain several basic amino acids. Any peptide sequence, or analogue thereof, which can be combined with a PNA and facilitates transport through the nuclear membrane can be used as an NLS according to the system of the present invention. The preferred method for testing whether or not a peptide comprises an NLS includes standard gene fusion protocols to insert a candidate NLS peptide into the sequence of a nucleic acid encoding a protein that normally is observed in the cytoplasm (see, e.g., Silver et al. (1984) Proc. Natl. Acad. Sci. U.S.A. 81:5951; Moreland et al. (1987) Mol. Cell. Biol. 7:4048; and Picard et al. (1987) EMBO J. 6:3333).

It is not necessary, however, to identify novel NLS peptides as numerous examples of functional NLSs are known to those with skill in the art. Example proteins that contain an NLS include: SV40 large T antigen (Lanford (1984) Cell 37:801–813), nucleoplasmin, polyoma virus large T, histones, and c-myc (U.S. Pat. No. 5,115,096 to Shoyab et al., incorporated herein by reference) MAX (U.S. Pat. No. 5,512,473 to Brent et al., incorporated herein by reference). Any peptide, derivative thereof, or peptide analogue that functions to transport an associated molecule through a nuclear membrane can be used for the present invention. Certain preferred specific NLSs include PKKKRKV (SEQ ID NO:3) which is a monopartite NLS from SV40 large T antigen, LVRKKRKTEEESPLKD-KDAKKSKQE (SEQ ID NO:2) which is a bipartite NLS from SV40 N1 protein (Dingwall et al., Trends Biochem Sci (1991) 16(12):478–81), and PEVKKKRKPEYP (SEQ ID NO:4) which is determined to function as an NLS by the inventor. The preferred embodiment of an NLS-PNA comprises an NLS characterized by the amino acid sequence LVRKKRKTEEESPLKDKDAKKSKQE (SEQ ID NO:2) linked by a peptide bond to a PNA characterized by the peptide nucleic acid sequence ACTGCCCA.

2.10 Membrane Transport Sequence (MTS)

A membrane transport sequence (MTS) functionally encompasses any peptide sequence, derivative thereof, or analogue that facilitates transport through the plasma membrane of a cell. Any such MTS peptide can be used according to the system of the present invention. Proteins or molecules that contain or are associated with an MTS, have been demonstrated to be transported into the cytoplasmic compartment of the cell (Lin U.S. Pat. No. 5,807,746, supra and Nadler U.S. Pat. No. 5,877,282, supra). The Lin and Nadler patents describe methods for screening for MTS peptides and provide examples of specific MTSs. A preferred MTS sequence comprises the amino acid sequence AAVALLPAV-LLALLAP (SEQ ID NO:1) which is derived from Kaposi fibroblast growth factor (K-FGF) (Lin U.S. Pat. No. 5,807, 746, supra). Another MTS is characterized by the amino acid sequence CFITKALGISYGRKKRRQRRRPPQGSQTH (SEQ ID NO:5) (Nadler U.S. Pat. No. 5,877,282, supra).

2.20 Peptide Nucleic Acid (PNA)

Peptide nucleic acids (PNAs) are a novel class of compounds that encompass nucleic acid analogues comprising ligands such as naturally occurring or synthetic DNA bases attached to a peptide backbone through a suitable linker (Nielsen U.S. Pat. No. 5,539,082, supra). Preferred PNAs carry the purine or pyrimidine bases of a nucleic acid attached to a peptide backbone in place of the typical pentose-phosphate backbone. Some characteristics of PNAs include that they are nuclease and protease resistant, can hybridize to nucleic acids, binds with higher affinity to complementary DNA than DNA itself, can displace a strand in duplex nucleic acids, and can modify expression in a positive or negative manner depending on the strand targeted, and especially in a promoter region (D. Y. Cherny et al. (1993) Proc. Natl. Acad. Sci. 90(5):1667–70; N. E. Mollegaard (1994) Proc. Natl. Acad. Sci. 91(9)3892–3895; P. E. Nielsen (1994) Gene 149(1):139–145; H. Orum (1995) Biotechniques 19(3):472–80). The binding of PNAs to single-stranded nucleic acid is essentially not affected by salt concentration (Cherny (1993) supra; Larsen et al., (1996) Nucleic Acids Res. (24) 458–463; Bentin et al. (1996) Biochemistry (35)8863–8869; and Wang et al., (1999) Nucleic Acids Res. (27)2806–2813).

In certain embodiments, the PNA comprises a sequence complementary to a region of a nucleic acid segment. In certain preferred embodiments, the PNA is annealed to the nucleic acid segment of the nucleic acid. A preferred PNA is targeted to 8 bases of the non-coding strand of the CMV promoter. The CMV sequence comprises the nucleic acid sequence TGGGCAGT. This preferred PNA sequence comprises the peptide nucleic acid oligomer ACTGCCCA. This PNA sequence was designed to hybridize to a CMV promoter which is utilized in numerous plasmid constructs, including pCMV-Luc which contains a luciferase reporter gene under the control of the CMV promoter (also referred to as pCMVLuc, herein) (for the CMV promoter see, U.S. Pat. No. 5,385,839 to Stinski, incorporated herein by reference and U.S. Pat. No. 5,168,062 to Stinski, incorporated herein by reference). By targeting the non-coding strand of the promoter, the PNA stimulates promoter function leading to increased expression of gene constructs inserted into the plasmid with the CMV promoter.

Additional PNA sequences will be readily apparent to those of skill in the art for the implementation of the present invention with the nucleic acid of choice including, but not limited to, plasmids, therapeutic vectors, expression vectors, or the like. PNA sequences that are complementary to a coding strand will typically inhibit expression of a targeted nucleic acid and PNA sequences that are complementary to a non-coding strand will typically stimulate expression of a targeted nucleic acid (N. E. Mollegaard, 1994; Good and Nielsen (1997) Antisense and Nucleic Acid Drug Development (7)431–7). PNA sequences comprising about two to about forty units in length are preferred according to the present invention. More preferred PNA sequences comprise about three to about twenty units in length. Still more preferred PNA sequences comprise about four to about 15 units in length. Still more preferred PNA sequences comprise about five to about ten units in length. The most preferred PNA sequences comprise about five, about six, about seven, about eight, about nine, or about ten units in length. In addition, PNA oligomers of about five to about eight, about 9 to about twelve, about 13 to about 15, and about 15 to about 20 units in length are useful. Any PNA, modified PNA, PNA analogue, or the like can be used according to the system of the present invention given that the PNA can be associated with an NLS, preferably by a peptide bond, and that at least a portion of the PNA can anneal to a nucleic acid sequence. PNAs of predefined sequence as well as random sequence PNAs are contemplated as being useful. PNA-nucleic acid chimeras and PNA-amino acid chimeras are also contemplated as being useful.

Additional PNA types, modifications, and analogues useful as a PNA according to the system of the present invention are described in the following U.S. Patents, each incorporated herein by reference.

U.S. Pat. No. 5,719,262 to Buchardt et al., describes PNAs having naturally-occurring nucleobases and non-naturally-occurring nucleobases attached to a polyamide backbone including amino acid (alkylamine) side chains. These PNAs are shown to have increased binding affinity to complementary DNA and RNA strands as well as increased sequence specificity and solubility.

U.S. Pat. No. 5,766,855 to Buchardt et al., describes the synthesis of PNAs containing at least one 2,6-diaminopurine nucleobase and at least one C1–C8 alkylamine side chain which have enhanced binding affinity and sequence specificity.

U.S. Pat. No. 5,714,331 to Buchardt et al., describes PNAs having enhanced binding affinity, sequence specificity and solubility. Methods of increasing specificity and binding affinity and solubility are provided.

U.S. Pat. No. 5,705,333 to Buchardt et al., describes nucleic acid mimetics referred to as "PENAMS" which have a peptidic backbone and nucleotidic sidechains that are capable of hydrogen bonding to complementary nucleic acid sequences. The use of PENAMS in antisense and target nucleic acid isolation is suggested.

U.S. Pat. No. 5,831,014 to Cook et al., and U.S. Pat. No. 5,539,083 to Cook et al., describe PNA combinatorial libraries and improved methods of synthesis of predefined PNA oligomers as well as random sequence PNA oligomers.

Additional PNA types, modifications, and analogues useful as a PNA according to the system of the present invention are described in the following International Patents.

International Patent WO 97/12995 describes kits for hybridization analysis with PNA probes.

International Patent WO 96/40709 describes PNA synthons that are compatible with DNA synthetic reagents and instrumentation and the use of the PNA synthons to create mixed PNA-DNA molecules referred to as PNA-DNA chimeras.

2.30 The Nucleic Acid

Any nucleic acid can be used in combination with the present invention. A useful nucleic acid encompasses any naturally occurring or synthetic nucleic acid, polynucleotide, derivative, or analogue thereof (analogues and modified bases are those specifically defined in WIPO Standard ST.25 (1998), supra). One with ordinary skill in the art will be able to determine which nucleic acid is useful and will be able to construct the useful nucleic acid. Sequence information for many useful nucleic acids is available in databases known to one with skill in the art (see for example, McKusick, Mendelian Inheritance in Man. Catalogs of Human Genes and Genetic Disorders. Baltimore: Johns Hopkins University Press (1998, 12th ed.); and Online Mendelian Inheritance in Man, OMIM Center for Medical Genetics, Johns Hopkins University (Baltimore, Md.) and National Center for Biotechnology Information, National Library of Medicine (Bethesda, Md.) (1999) World Wide Web URL: "http://www.ncbi.nlm.nih.gov/omim"). Alternatively, many useful nucleic acids are commercially available. In addition, one with ordinary skill in the art is able to determine the sequence of a region of nucleic acid using methods known in the art. In certain embodiments, the PNA is synthesized with a sequence that is complementary to a region of the nucleic acid or nucleic acid segment.

The nucleic acid can be, but is not limited to, single-stranded nucleic acid, double-stranded nucleic acid, polynucleotides, DNA, RNA, and single- or double-stranded viral nucleic acid. In certain preferred embodiments, the nucleic acid comprises an expression vector. The expression vector can include a gene sequence under the control of a promoter region which one with skill in the art can design to be compatible with a host cell, such that, the gene is expressed after transfer into the nucleus. The transfer step is carried out according to methods disclosed in the present invention. In certain embodiments, the nucleic acid can be a plasmid, a circular nucleic acid, a linear nucleic acid, a viral vector, a therapeutic vector, and the like.

In certain embodiments, the nucleic acid comprises an antisense nucleic acid targeted to complementary sequences in the nucleus. Specifically, the bridging of introns, exons, and intron-exon boundaries is contemplated with antisense strands or antisense encoding vectors. In certain embodiments, the nucleic acid encodes an expression product, wherein the expression product comprises a peptide, a polypeptide, a protein, a fusion protein, or an antisense nucleic acid. In certain embodiments, an NLS-PNA (or an MTS-NLS-PNA as described herein) has an antisense activity, wherein the antisense activity is localized in the nucleus, not in the cytoplasm, because the NLS directs the complex to the nucleus and retains it in the nucleus. U.S. Pat. No. 5,700,922 to Cook, incorporated herein by reference; describes the use of PNA-DNA-PNA chimeras in non-nuclear antisense reactions. In certain embodiments wherein an antisense nucleic acid is expressed from a nucleic acid annealed to an NLS-PNA (or an MTS-NLS-PNA as described herein), the antisense reaction can take place in any compartment of a cell or even outside of a cell. In certain embodiments, the nucleic acid encodes a gene, a reporter gene, a gene fusion, a transgene, or a therapeutic gene. A particularly useful nucleic acid, comprises a double-stranded expression vector with an insert under the control of a cytomegalovirus (CMV) promoter. The preferred PNA sequence, for use with this nucleic acid, comprises the peptide nucleic acid oligomer ACTGCCCA which is complementary to a region on the non-coding strand in the area of the CMV promoter. The annealed PNA stimulates transcription directed by the CMV promoter.

In certain embodiments, the nucleic acid is a therapeutic vector (including plasmid, expression, viral, and the like) capable of expressing a therapeutic gene in the host cell (the cell into which the therapeutic vector is transferred). It is preferred that the therapeutic vector express the therapeutic gene product either constitutively or inducibly in the host cell. The PNA can be annealed to the non-coding strand of a promoter having control over the expression of the gene product, wherein such design stimulates expression. The therapeutic vector can comprise a DNA vaccine. In certain embodiments, the therapeutic gene comprises alpha 1-antitrypsin, CFTR, cox-1, cox-2, p53 protein, adenosine deaminase, phenylalanine hydroxylase, apolipoprotein E, apolipoprotein AI, insulin, epidermal growth factor, transforming growth factor-beta, insulin-like growth factor-1, insulin-like growth factor-2, transforming growth factor beta, or insulin-like growth factor binding proteins. In other embodiments, the gene comprises a reporter gene including chloramphenicol transferase, luciferase, beta-galactosidase, or green fluorescent protein.

3.00 Synthesis of an NLS, an MTS, a PNA, and Combinations Thereof

Methods for the synthesis of peptides, polypeptides, and proteins are well known to those of skill in the art using biological, enzymatic, and chemical means.

The preferred method of synthesizing the NLS and the MTS according to the present invention is by solid phase peptide synthesis which is known to one with skill in the art (see B. Merrifield (1997) Methods Enzymology 289:3–11; G. Barany et al., The Peptides: Analysis, Synthesis, Biology, Gross et al., Vol. 2, Academic Press, New York, (1980), pp. 3–254). Solid phase peptide synthesis is described in the following U.S. Patents, each incorporated herein by reference: U.S. Pat. No. 5,373,053 to Berg et al.; U.S. Pat. No. 5,258,454 to Berg et al.; U.S. Pat. No. 4,507,230 to Tam et al.; and U.S. Pat. No. 4,631,211 to Houghten.

In general, solid phase synthesis methods comprise the sequential addition of one or more specific amino acids or suitably protected specific amino acids to a growing peptide chain. Either a first amino acid or capping group is attached to an insoluble support contained within a reaction vessel. A second amino acid or derivative with either a protected amino or carboxyl group and a complementary reactive group (carboxyl or amino) is reacted with the first amino acid or capping group under conditions suitable for forming the amide linkage. The protecting group is then chemically removed and the next amino acid residue with a protecting group is coupled in a similar fashion. A peptide of defined sequence is thus generated by sequential addition. After all of the desired amino acids have been linked in the proper sequence, any remaining protecting groups and any solid support are removed either sequentially or concurrently to afford the final polypeptide. By simple modification of this general procedure, it is possible to add more than one amino acid at a time to a growing chain, for example, by coupling (under condition that do not racemize chiral centers) a protected tripeptide with a properly protected dipeptide to form, after deprotection, a pentapeptide.

Typical protecting groups include t-butyloxycarbonyl (Boc), 9-fluorenylmethoxycarbonyl (Fmoc), benxyloxycarbonyl (Cbz), p-toluenesulfonyl (Tos); 2,4-dinitrophenyl, benzyl (Bzl), biphenylisopropyloxy-carboxycarbonyl, cyclohexyl, isopropyl, acetyl, o-nitrophenylsulfonyl, and the like. Of these, Boc and Fmoc are preferred. Typical solid supports are generally cross-linked polymeric materials. These include divinylbenzene cross-linked styrene-based polymers, for example, divinylbenzene-hydroxymethylstyrene copolymers, divinylbenzene-chloromethylstyrene copolymers, and divinylbenzene-benzhydrylaminopolystyrene copolymers. In one method, the polypeptides are prepared by conventional solid phase chemical synthesis on, for example, an Applied Biosystems, Inc. (ABI) 430A peptide synthesizer using a resin that permits the synthesis of the amide peptide form and using t-Boc amino acid derivatives (Peninsula Laboratories, Inc.) with standard solvents and reagents. Polypeptides containing either L- or D-amino acids may be synthesized in this manner, also. Polypeptide composition is confirmed by quantitative amino acid analysis and the specific sequence of each peptide may be determined by sequence analysis using standard methods known to those of ordinary skill in the art.

Methods for the synthesis of peptide nucleic acids are known to those with ordinary skill in the art. The preferred method for synthesis of the PNA also involves solid phase synthesis and is described in detail in U.S. Pat. No. 5,539, 082 to Nielsen, supra. Improvements in the method of PNA synthesis including PNA-peptide chimeras and improvements in nucleic acid binding specificity and affinity are described in the following U.S. Pat. Nos. 5,719,262, supra; U.S. Pat. No 5,766,855, supra; U.S. Pat. No 5,714,331, supra; U.S. Pat. No 5,705,333, supra; U.S. Pat. No 5,831, 014, supra; U.S. Pat. No 5,539,083, supra. It is preferred that an NLS-PNA and an MTS-NLS-PNA are synthesized according to the principles of solid phase synthesis which results in sequences of amino acids and peptide nucleic acid residues linked by amide bonds. Any combination of MTS, NLS, and PNA can be synthesized by specifying the addition of amino acids and peptide nucleic acids to the growing chain.

The newly synthesized peptide-PNA may be substantially purified by preparative high performance liquid chromatography (e.g., T. Creighton Proteins, Structures and Molecular Principles (1983), W. H. Freeman and Co., New York, N.Y.). The composition of the synthetic peptides may be confirmed by amino acid analysis or sequencing (e.g., the Edman degradation procedure; Creighton, supra). Additionally, the amino acid sequence of the peptide, or any part thereof, may be altered during direct synthesis and/or combined using chemical methods with sequences from other proteins, or any part thereof, to produce a variant polypeptide/PNA. This includes peptide mimetics which functionally mimic the NLS, MTS, or PNA described above. Mimetic design will be apparent to those of skill in the art and aspects of mimetic design are described in U.S. Pat. No. 5,877,282 to Nadler, supra.

3.10 Production of a Nucleic Acid

Many desirable vectors, plasmids, expression vectors, DNAs, RNAs, oligonucleotides, strands of nucleic acid, and the like are readily available through commercial sources and are useful in certain embodiments of the present invention as a nucleic acid (e.g., Roche, Stratagene, In Vitrogene, Promega, PerSeptive Biosystems, Research Genetics, and the like). Also, a nucleic acid can be produced by techniques of molecular biology known to those of ordinary skill in the art (see e.g., Sambrook et al., Molecular Cloning: A Laboratory Manual, Second Edition (1989) Cold Spring Harbor Laboratory Press). The meaning of terms such as "expression vector", "vector", "expression construct", or "construct" that are used in certain embodiments, are known to those of ordinary skill in the art. The terms "expression vector", "vector", "expression construct", or "construct" are used interchangeably and, in general, refer to any nucleic acid that encodes an expression product. The terms "expression vector", "vector", "expression construct", as, or "construct" are also known to one with skill in the art. In certain embodiments, the nucleic acid is expressed. In certain embodiments, the expression product includes a binding product, wherein the binding product anneals to a complementary nucleic acid. In certain embodiments, at least a portion of the expression product is capable of being transcribed. In certain preferred embodiments, the resulting transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

Particularly useful vectors are contemplated to be those vectors in which a coding portion of the DNA segment, whether encoding a full length protein, polypeptide or smaller peptide, is positioned under the transcriptional control of a promoter. In certain aspects "promoter" refers to a DNA sequence recognized by the synthetic machinery of the cell, or introduced synthetic machinery, required to initiate the specific transcription of a gene. The phrases "operatively positioned", "under control" "regulates", or "under transcriptional control" include the meaning that the promoter is in the correct location and orientation in relation to the nucleic acid to control RNA polymerase initiation and expression of the gene. These terms are known to one of ordinary skill in the art.

The promoter may be in the form of the promoter that is naturally associated with a gene, as may be obtained by isolating the 5' non-coding sequences located upstream of the coding segment or exon, for example, using recombinant cloning and/or PCR™ technology (PCR™ technology is disclosed in U.S. Pat. No. 4,683,202 to Mullis; U.S. Pat. No. 4,683,195 to Mullis et al.; U.S. Pat. No. 4,800,159 to Mullis et al.; U.S. Pat. No. 4,965,188 to Mullis et al.; U.S. Pat. No. 5,656,493 to Mullis et al.; each patent incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a gene in its natural environment. Such promoters may include promoters normally associated with other genes, and/or promoters isolated from any other bacterial, viral, eukaryotic, or mammalian cell, and/or promoters made by the hand of man that are not "naturally occurring," i.e., containing difference elements from different promoters, or mutations that increase, decrease, or alter expression.

Naturally, it will be important to employ a promoter that effectively directs the expression of the DNA segment in the cell type, organism, or animal, chosen for expression. The use of promoter and cell type combinations for protein expression is generally known to those of skill in the art of molecular biology (for example, see Sambrook et al. (1989), supra). The promoters employed may be constitutive, or inducible, and can be used under the appropriate conditions to direct high level as expression of the introduced DNA segment, such as is advantageous in the large-scale production of recombinant proteins or peptides.

At least one module in a promoter generally functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to, fix the place of initiation.

Additional promoter elements regulate the frequency of transcriptional initiation. Typically, these are located in the region about 30–110 base pairs upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 base pairs apart before activity begins to decline. Depending on the promoter, it appears that individual elements can function either cooperatively or independently to activate transcription.

In certain embodiments, the particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. In other embodiments, a particular promoter that directs expression to a certain tissue or allows for regulation of expression by an additional control element may be desired. The selection and use of such particular promoters will be apparent to those with skill in the art (see, e.g., U.S. Pat. No. 5,858,774 to Malbon et al., incorporated herein by reference; Gene-Expression Systems (1998) Fernandez et al., eds. Academic Press; M. Kriegler, Gene Transfer and Expression: A Laboratory Manual (1991) Oxford University Press; and Gene Expression: General and Cell Type Specific (1993) M. Karin (ed.) Birkhauser).

In various embodiments, the human cytomegalovirus (CMV) immediate early gene promoter, the SV40 early promoter, and the Rous sarcoma virus long terminal repeat can be used to obtain high-level expression of the nucleic acid. The use of other viral or mammalian cellular promoters which are well-known in the art to achieve expression are contemplated as well, provided that the levels of expression are sufficient for a given purpose. Elements and promoters from the following genes and viral genomes may be useful, in the context of the present invention, to regulate the expression of a gene: β-Actin, metallothionein, H2B (TH2B) histone, mouse or type I collagen, SV40 promoter, polyoma promoter, retroviral promoters, papilloma virus, hepatitis B virus, human immunodeficiency virus, and cytomegalovirus. Inducible elements and promoter can be derived from the following genes and viral genomes with the inducing agent in parentheses: MT II (phorbol ester (TFA) and heavy metals), mouse mammary tumor virus (MMTV, stimulated by glucocorticoids), adenovirus 5 E2 (Ela), and SV40 (TPA). These lists are not intended to be exhaustive of all the possible useful elements involved in the promotion of expression, but they are exemplary thereof.

Enhancers were originally detected as genetic elements that increased transcription from a promoter located at a distant position on the same molecule of DNA. They are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter has one or more elements that direct initiation of RNA synthesis at a particular site and in a particular orientation, whereas enhancers lack such specifics. Promoters and enhancers are often overlapping and contiguous, often seeming to have a very similar modular organization. Additionally any promoter and enhancer combination could also be used to drive expression. Additional promoters and enhancers are described in the Eukaryotic Promoter Database (Rouaïda Cavin Périer et al. (1999) Nuc Acid Res 27:307–309 and located on the World Wide Web at URL: "http//www.epd.isb-sib.ch").

3.20 Annealing of a PNA and a Nucleic Acid

Methods for annealing a PNA to a nucleic acid are known to those of ordinary skill in the art and are described in U.S. Pat. No. 5,539,082, supra; U.S. Pat. No. 5,539,083, supra; U.S. Pat. No. 5,714,331, supra; and U.S. Pat. No. 5,766,855, supra. The preferred method is as follows and is also meant to include the preferred method for the annealing of an MTS-NLS-PNA and a nucleic acid. An NLS-PNA is synthesized with a PNA of about 8 peptide nucleic acid units in length. The NLS-PNA is mixed with the nucleic acid in a suitable biological carrier. The mixture is heated for an effective period of time and at an effective temperature for promoting access of the PNA portion of the composition to a complementary region of the nucleic acid. The mixture is cooled at an effective rate and to an effective temperature for promoting stability of the PNA/nucleic acid complex.

A "suitable biological carrier" is meant to include, but is not limited to: water or a solution of about ten millimolar tris and one millimolar EDTA (T10E1), a solution of T10E1 further comprising less than about ten millimolar salt, a solution of T10E1 further comprising less than about 50 millimolar salt, or any other solution in which peptides and peptide nucleic acids can be dissolved and annealed. A preferred biological carrier is a solution of T10E1 with essentially no salt. In general, PNAs are characterized to have a higher binding affinity for complementary double-stranded nucleic acids in low salt or in the absence of salt compared to higher salt conditions. Higher salt conditions are considered herein to be similar to those found in a cell or higher. This does not mean that PNAs will not bind to a complementary nucleic acid sequence in the presence of salt. It simply means that the binding affinity is reduced at the higher salt concentrations. This can be overcome by increasing the PNA concentration in the annealing reaction. Once annealed, it is known that the PNA to nucleic acid interaction is stable in any salt concentration including physiological conditions and in more than one molar salt. The annealing of PNAs to single-stranded nucleic acids is essentially not affected by salt concentration including salt concentrations in the physiological range.

Any amount of time that allows the NLS-PNA or MTS-NLS-PNA to physically associate with the nucleic acid could be used. One time parameter for the heating step comprises from about one second to about twenty-four hours. A more preferred time parameter for the heating step comprises from about fifteen minutes to about two hours. A still more preferred time parameter for the heating step comprises from about thirty minutes to about ninety minutes. A highly preferred time parameter for the heating step comprises about sixty minutes.

Any temperature that allows the NLS-PNA or MTS-NLS-PNA to physically associate with the nucleic acid could be used. One temperature parameter for the heating step comprises from about twenty degrees centigrade to about one-hundred degrees centigrade. A more preferred temperature parameter for the heating step comprises from about forty degrees centigrade to about eighty degrees centigrade. A still more preferred temperature parameter for the heating step comprises from about forty-five degrees centigrade to about sixty degrees centigrade. A highly preferred temperature parameter for the heating step comprises about fifty degrees centigrade.

The preferred time and temperature parameters for the heating step will vary in relationship to one another. For example, a longer period of heating will generally be helpful at lower temperatures. Also, the period of heating can be shortened generally at higher temperatures. Preferred time and temperature parameters for the heating step are about sixty minutes at about fifty degrees centigrade for a preferred PNA oligomer of about eight units in length. Useful parameters can be determined readily by one with skill in the art.

The heating step can be carried out in any suitable reaction vessel. A preferred vessel is a polypropylene Eppendorf tube, with cap, common to most laboratories. The heat source can be derived from any acceptable heat source. A preferred heat source would be a water bath or a shaking water bath maintained at a preferred heating temperature. An alternative preferred heat source would be a thermocycler common to most laboratories.

The mixture is cooled to an effective second temperature over an effective second period of time for promoting annealing of the PNA and nucleic acid. An annealing temperature comprises from about minus twenty degrees centigrade to about fifty degree centigrade. A more preferred annealing temperature comprises from about ten degrees centigrade to about thirty degrees centigrade. A still more preferred annealing temperature comprises about twenty degrees centigrade. A highly preferred annealing temperature comprises about room temperature, wherein room temperature generally includes about nineteen, about twenty, about twenty-one, about twenty-two, about twenty-three, or about twenty-four degrees centigrade. A second period of time for annealing comprises about one second to about seventy-two hours. A preferred period of time for annealing comprises about twelve hours to about thirty-six hours. A more preferred period of time for annealing comprises about twenty-four hours.

It is highly preferred that the temperature is decreased gradually over this period of time which promotes efficient annealing of the PNA and the nucleic acid. A gradual temperature change is achieved using a programmable thermocycler or by simply turning off the water bath containing several gallons of water and letting the bath go to room temperature over time. Once annealed, the PNA oligomer and nucleic acid hybrid are stable in physiological conditions. The heating time and temperature and cooling rate and temperature will depend on the length of the PNA and can be readily determined by one with skill in the art.

4.00 Transfer Into the Nucleus of a Cell

The terms "transformation" and "transfection" are well known to one with ordinary skill in the art. The term "transformation" generally refers to the introduction of a nucleic acid into a prokaryotic cell. The term "transfection" generally refers to the introduction of a nucleic acid into a eukaryotic cell. The terms "transformation" and "transfect" are specifically defined herein to also encompass the introduction of compositions other than nucleic acids into a cell including compositions such as peptides and peptide nucleic acids.

Standard transfection procedures for transferring and expressing an exogenous nucleic acid in a cell in the prior art relied on rare events such as dissolution of the nuclear membrane in order for the nucleic acid to become localized in the nucleus wherein key components of the cellular expression machinery resides. In the present invention, an NLS-PNA or an NLS-PNA-NA can be transfected into the cytoplasm of the cell using essentially any means known in the art including: liposome-mediated, chemical, physical, and other means. Alternatively, an MTS can be included in the composition which will cause translocation across the cytoplasmic membrane. Once in the cytoplasm, the NLS will direct the composition into the nucleus and maintain a nuclear localization of the composition.

Important to NLS-PNA-NA transfections is that the PNA to nucleic acid hybridization is a strong interaction. The PNA to nucleic acid hybridization can be disrupted, but it generally takes incubation at a temperature of about 50C or more for about 2 hours, or incubation in a highly basic buffer for about 30 minutes or more, to fully separate the molecules. These conditions are representative of a 8 base interaction between a PNA and a nucleic acid. Additional conditions and conditions for sequences of varying length are readily determined by one with skill in the art. The conditions mentioned above are not normally present in living cells. Therefore, the nucleic acid remains bound to the PNA and the nucleic acid is transported into the nucleus by the NLS which is combined with the PNA.

4.10 Non-Viral Transfection Methods

Transfection procedures can be divided into viral and non-viral methods. In general, non-viral transfection methods are preferred over viral transfection methods according to the system of the present invention. Numerous non-viral transfection methods are known to those of skill in the art (see, e.g., Gene Transfer and Expression Protocols (Methods in Molecular Biology, VOL 7) (1991) E. J. Murray (ed.) Humana Press; M. Kriegler, Gene Transfer and Expression: A Laboratory Manual (1991) Oxford University Press). In addition, there are numerous commercially available transfection kits (e.g., Stratagene, InVitrogen, Roche, and the like). Some non-viral transfection methods are described below. They are not meant to limit the scope of the present invention, but, merely to be exemplary thereof. In addition to in vitro use, these transfection techniques may be utilized in vivo or ex vivo, as discussed below and disclosed in U.S. Pat. No. 5,858,784 to R. J. Debs et al., incorporated herein by reference. U.S. Pat. No. 5,580,859 to Felgner et al., incorporated herein by reference; describes the combination of several of the transfection methods mentioned below with direct injection into muscle and tissues.

4.11 MTS Mediated Transfection

In certain embodiments, the membrane transport sequence (MTS) functions as a transfection agent. It is demonstrated that when a cell is contacted with a composition linked to an MTS, the entire MTS linked composition translocates through the cytoplasmic membrane of a cell (as described in Lin, U.S. Pat. No. 5,807,746, supra). Thus, in certain embodiments, the MTS portion of an MTS-NLS-PNA or an MTS-NLS-PNA-NA directs a translocation or "transfection" across the cytoplasmic membrane of a cell and into the cytoplasmic compartment. MTS mediated transfection is an exemplary method of translocating a composition of the present invention across a cytoplasmic membrane.

4.12 Liposome Mediated Transfection

Liposome mediated transfection is another exemplary embodiment for a method of introducing compositions of the present invention into a cytoplasmic compartment of a cell. Liposome and lipid based methods are readily known to those of skill in the art and numerous kits are available commercially (see e.g., Liposome Technology: Liposome Preparation and Related Techniques (1992) G. Gregoriadis (ed.) CRC Press; U.S. Pat. No. 5,279,833 to Rose, incorporated herein by reference; U.S. Pat. No. 5,567,433 to Collins, incorporated herein by reference; U.S. Pat. No. 4,515,736 to Deamer, incorporated herein by reference; Fefgner et al., (1987) Proc. Nat. Acad. Sci., USA 84:471–477; and Gao et al (1991) Biochem. Biophys. Res. Comm. 179:280–285). Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. A commercially available liposomal transfection reagent is Lipofectamin™ (DOTMA:DOPE by Gibco-BRL).

Liposome-mediated nucleic acid delivery and expression of foreign DNA in vitro has been successful with demonstrated liposome-mediated delivery and expression of foreign DNA in cultured chick embryo, HeLa, and hepatoma cells. In certain embodiments of the present invention, the liposome may be complexed with a hemagglutinating virus (HVJ). This has been shown to facilitate fusion with the cell membrane and promote cell entry of liposome-encapsulated DNA. In other embodiments, the liposome may be complexed or employed in conjunction with nuclear non-histone chromosomal proteins (HMG-1). In yet further embodiments, the liposome may be complexed or employed in conjunction with both HVJ and HMG-1. In other embodiments, the delivery vehicle may comprise a ligand and a liposome to target the liposome to particular cell types or tissues U.S. Pat. No. 5,059,421 to Loughrey et al., describes a general method of attaching protein molecules to liposomes to achieve well-characterized, sized protein-liposome conjugate systems for interchangeable targeting applications. Using the system of U.S. Pat. No. 5,059,421; one with skill in the art can design a pharmaceutical liposomal composition for delivery of a composition of the present invention (for example, an NLS-PNA and/or an NLS-PNA-NA). This pharmaceutical liposomal composition can be targeted to essentially any cell type or tissue, if desired. U.S. Pat. No. 4,885,172 to Bally et al., describes compositions and methods for storing liposomes including targeted liposomes and the loading of the such liposomes on an "as needed" basis. U.S. Pat. No. 5,059,421 and U.S. Pat. No. 4,885,172 are hereby incorporated herein by reference.

U.S. Pat. No. 5,851,818 to Huang et al., incorporated herein by reference; discloses improved methods for preparing nucleic acid/liposome complexes including selection of the working medium and liposome lipid to nucleic acid ratios.

U.S. Pat. No. 5,279,883 to Rose, incorporated herein by reference; describes liposomal transfection of nucleic acids into animal cells. Compositions of the present invention can be essentially substituted for the nucleic acids in U.S. Pat. No. 5,279,883 for transfer into the cytoplasmic compartment of animal cells. The NLS of compositions of the present invention will deliver the instant compositions into the nuclear compartment.

U.S. Pat. No. 5,225,212 to Martin, incorporated herein by reference; describes a liposome composition for extended release of a therapeutic compound into the bloodstream and methods for use thereof.

4.13 Electroporation

In certain embodiments a composition of the present invention is introduced into a cell via electroporation. Electroporation involves the exposure of a suspension of cells and the composition to a high-voltage electric discharge (see U.S. Pat. No. 4,956,288 to Barsoum, incorporated herein by reference). Transfection of nucleic acids into eukaryotic cells using electroporation is quite successful. Mouse pre-B lymphocytes are transfected with human kappa-immunoglobulin genes, and rat hepatocytes are transfected with the chloramphenicol acetyltransferase gene in this manner.

4.14 Calcium Phosphate or DEAE-Dextran

In certain embodiments a composition of the present invention is introduced into a cell using calcium phosphate precipitation. Transfection with calcium phosphate is described in U.S. Pat. No. 5,633,156 to Wurm et al., incorporated herein by reference. Human KB cells are transfected with adenovirus 5 DNA using this technique. Also in this manner, mouse L(A9), mouse C127, CHO, CV-1, BHK, NIH3T3 and HeLa cells are transfected with a neomycin marker gene, and rat hepatocytes are transfected with a variety of marker genes and in another embodiment, the expression construct is delivered into the cell using DEAE-dextran followed by polyethylene glycol. In this manner, reporter plasmids are introduced into mouse myeloma and erythroleukemia cells.

4.15 Particle Bombardment

In an alternative embodiment, a composition of the present invention is introduced into a cell by methods that include particle bombardment. This method depends on the ability to accelerate nucleic acid-coated microprojectiles to a high velocity allowing them to pierce cell membranes and enter cells without killing them. Several devices for accelerating small particles have been developed. One such device relies on a high voltage discharge to generate an electrical current, which in turn provides the motive force. The microprojectiles used have consisted of biologically inert substances such as tungsten or gold beads.

4.16 Direct Microinjection or Sonication Loading

In certain embodiments, a composition of the present invention is introduced into a cell by direct microinjection or sonication loading. Direct microinjection has been used to introduce nucleic acid constructs into Xenopus oocytes, and LTK⁻ fibroblasts have been transfected with the thymidine kinase gene by sonication loading. Current methods for the introduction of nucleic acids into an early embryo or morula for the creation of transgenic animals typically involves direct microinjection of the nucleic acid (see U.S. Pat. No. 5,225,750 to Higuchi et al., incorporated herein by reference). Certain embodiments of the present invention supersede microinjection technology by allowing other means of introducing a nucleic acid into the nucleus of cells in an early embryo or morula. For example, a composition comprising an NLS-PNA, wherein the sequence of the PNA is complementary to a region of the nucleic acid of interest, can be annealed to the nucleic acid of interest, incorporated into a liposome (for example) and efficiently transfected into the nuclear compartment of the embryo cells without a microinjection step. In another example, the early embryo or morula is directly contacted by an MTS-NLS-PNA-NA to achieve transfection of the nucleic acid into the nuclear compartments of the cells. It is envisioned that NLS-PNA mediated nucleic acid transfer can be accomplished in vivo for the creation of transgenic animals without a microinjection step.

4.17 Adenoviral Assisted Transfection

In certain embodiments of the present invention, the expression construct is introduced into the cell using adenovirus assisted transfection. Increased transfection efficiencies have been reported in cell systems using adenovirus coupled systems (see U.S. Pat. No. 5,928,944 to Seth et al., incorporated herein by reference; and U.S. Pat. No. 5,830,730 to German et al., incorporated herein by reference).

5.00 Regulation of Expression and Antisense

The meaning of the term "antisense" nucleic acid is known to one of ordinary skill in the art and refers to a nucleic acid which can hybridize to another nucleic acid or to a nucleic acid construct or vector that encodes an antisense nucleic acid. Typically, there is a degree of complementary homology between an antisense nucleic acid and its target nucleic acid. As specifically defined herein, an antisense reaction can also include PNA oligomer to nucleic acid hybridization.

Methods for the application of antisense technology are known to one of ordinary skill in the art. Treatment of cancer in a human using antisense technology is described in U.S. Pat. No. 5,087,617 to Smith, incorporated herein by A reference. Antisense RNA constructs, or DNA encoding such antisense RNAs, may be employed to inhibit specific or desired gene transcription or translation or both within the cells of the present invention. Antisense nucleic acids may be designed to bind to the promoter and other control regions, exons, introns, or intron-exon boundaries of a gene. Antisense RNA constructs, or DNA encoding such antisense RNAs, may be employed to inhibit gene transcription or translation or both within a host cell, either in vitro or in vivo, such as within a host animal, including a human subject.

Compositions of the present invention, including an NLS-PNA and an MTS-NLS-PNA, can be used to regulate an expression of a target nucleic acid segment in the nucleus of a cell through annealing of the PNA portion of the NLS-PNA to the target nucleic acid. In terms of antisense regulation of expression, one way in which the present invention differs from previous disclosures in that the antisense reaction in the present invention is localized within the nucleus. The NLS directs the antisense reaction to the nuclear compartment and maintains a nuclear localization of any bound complex.

Regulation of expression by the annealed NLS-PNA can be either positive regulation or negative regulation. For example, when binding to RNA, the NLS-PNA may prevent the RNA from being properly spliced and block transport of the RNA out of the nucleus which prevents expression of the RNA. When the NLS-PNA binds to the non-coding strand of a gene, the NLS-PNA increases expression of the gene, especially when targeted to the 5' untranslated region of the gene. When the PNA binds to the coding strand of a gene, the NLS-PNA will decrease expression of the gene. It is contemplated that a multi-segment PNA can be combined with the NLS, such that the NLS-PNA will bind to the same complementary segment of multiple nucleic acids or to different complementary segments of the same nucleic acid. For example, it may be desirable to anneal a multi-segment PNA to different parts of an RNA or a gene to create looped structures held together by a PNA backbone.

Compositions of the present invention including an NLS-PNA can also be used to deliver a nucleic acid into the nuclear compartment of a cell as described herein. Antisense constructs can be expressed from the transferred nucleic acid wherein the antisense expression products influence cellular events in the nucleus, in the cytoplasm, or even outside of the cell. In certain embodiments compositions including an NLS-PNA are used in vitro, in vivo, or ex vivo. It is further contemplated that an NLS-PNA (including an NLS-PNA-NA or composition containing an MTS) can be used with a nuclear extract, a nucleated cell, a yeast cell, an insect cell, a plant cell, an animal cell, as a therapy, and as a therapy for a human condition or disease.

5.10 Ribozymes

Another method for inhibiting an expression of a gene contemplated in the present invention is via ribozymes (U.S. Pat. No. 4,987,071 to Cech et al., incorporated herein by reference). Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity. For example, a large number of ribozymes accelerate phosphoester transfer reactions with a high degree of specificity, often cleaving only one of several phosphoesters in an oligonucleotide substrate. The ribozyme can be transferred into the nucleus of a cell using an NLS-PNA wherein the PNA is complementary to and annealed to a portion of the ribozyme.

5.20 Homologous Recombination

In certain embodiments, it is contemplated that compositions of the present invention, for example an NLS-PNA, are used to deliver vectors specifically designed for use in the method of homologous recombination. Methods for homologous recombination are known to those with skill in the art and disclosed in the following U.S. Patents, each incorporated herein by reference: U.S. Pat. No. 5,468,629 to Calhoun; U.S. Pat. No. 5,413,923 to Kucherlapati et al.; U.S. Pat. No. 5,416,260 to Koller et al.; U.S. Pat. No. 5,612,205 to Kay et al.; U.S. Pat. No. 5,721,367 to Kay et al.; and U.S. Pat. No. 5,615,396 to Bradley et al. The Calhoun U.S. Pat. No. 5,468,629 patent, supra, describes the use of nucleoprotein complexes for transfection and homologous recombination. The method of Calhoun specifies that the cell undergo mitosis, however.

Uses for homologous recombination techniques include the precise modification of existing genes, the inactivation of specific genes, and the replacement of one gene for another. Homologous recombination is used in the art in the production of transgenic animals.

5.30 Transfection

Compositions of the present invention can be used for the efficient transfection of eukaryotic cells. An NLS-PNA can be annealed to a complementary region on a nucleic acid forming an NLS-PNA-NA. The interaction between the PNA and the nucleic acid is stable in many environments including physiological conditions in and around a cell. The NLS-PNA-NA can be transfected into the cytoplasm of the eukaryotic cell using standard methods described above.

Transfection compositions and methods in the prior art do not provide for the efficient transfer of the nucleic acid from the cytoplasmic compartment, through the nuclear membrane, and into the nuclear compartment. Previous methods relied mainly on the dissolution of the nuclear membrane during mitosis during which time, the nucleic acid might distribute throughout the volume of the cell. After the membrane reforms, some nucleic acid might be trapped in the nucleus. However, these previous methods provided a low percentage of successful transfection events, on the order of about 3% or less for rapidly dividing cells. Furthermore, the expression of the transferred nucleic acid was quenched rapidly within 3 or 4 days, in the prior art, due to transport of the transfected nucleic acid back out of the nucleus.

In the present invention, the PNA holds the nucleic acid securely to the NLS-PNA and the NLS provides direct, active transport from the cytoplasm into the nuclear compartment of the eukaryotic cell. Furthermore, the nucleic acid is retained in the nucleus through the activity of the NLS. Importantly, the PNA/nucleic acid interaction does not damage the nucleic acid which could prevent expression. In fact, the PNA/nucleic acid interaction can be used to regulate expression of the nucleic acid as described herein.

In certain embodiments, an MTS moves an MTS-NLS-PNA or an MTS-NLS-PNA-NA through the cytoplasmic membrane into the cytoplasmic compartment after putting the complex in contact with the cell. The NLS then transports the complex into the nuclear compartment.

The present invention makes possible the transfection of previously refractory cells types. Previously refractory cell types include, but are not limited to, essentially non-dividing cells, quiescent cells, cells with a long doubling time (more than about twenty-four hours), terminally differentiated cells, nucleated cells, embryonic stem cells. Even the majority of cells with a doubling time of less than about twenty-four hours have an intact nucleus. Therefore, the compositions and methods of the present invention have application in improving transfection efficiency in "rapidly dividing cells".

The strength of the PNA/nucleic acid interaction is evidenced by a melting temperature of about 45° C. to about 55° C. for a PNA that is about eight bases in length and annealed to a nucleic acid compared to a melting temperature of less than 30° C. for a nucleic acid to nucleic acid hybrid of similar length (Good and Nielsen (1997), supra). Thus, nucleic acid to nucleic acid hybrids of eight bases in length dissociate under physiological conditions. In certain preferred embodiments, the NLS-PNA is annealed to double-stranded nucleic acid in vitro under conditions that promote annealing. Once annealed, the NLS-PNA-NA complex remains essentially intact under physiological conditions. The NLS, MTS, and PNA elements in a composition can be arranged in any order. In certain embodiments, if a nucleic acid is present in a composition, then the nucleic acid and the PNA will be associated.

It is contemplated that diverse nucleic acids will be utilized according to the system of the present invention including: specific nucleic acids, random nucleic acids, or multiple nucleic acids. For example, in one embodiment, the alpha-1 antitrypsin (AAT) gene is transfected into human lung cells using an NLS-PNA. In another example, random nucleic acids generated by methods known in the art are transfected into cells using PNAs (the PNAs are also of random sequence and generated by methods known in the art) as a means of fastening the random nucleic acids for transfer into the nucleus. In still another example, fragments of nucleic acid, preferably encompassing an entire genome, are transfected into cells in an approach known in the art as "shotgun cloning". In yet another example, multiple genes are transfected with multiple NLS-PNAs. Also, multiple nucleic acids can be annealed to an NLS-PNA wherein the PNA is multi-segmented. Such embodiments could be used to treat a multi-genetic disorder.

The system of the present invention is not limited to nucleic acids of known sequence because a nucleic acid of interest can be sequenced using methods known to those with skill in the art without undue experimentation. Furthermore, the sequence of a major portion of the human genome has been determined and the sequences of several other organisms are completely known. Known sequence can be found in databases known to one with skill in the art. Still further, a nucleic acid of unknown sequence can be cloned into vectors of known sequence, using standard methods known to those with ordinary skill in the art. These vectors can then be used for sequencing the unknown portion, or directly utilized in certain embodiments of the present invention.

5.40 Gene Therapy

The present invention is envisioned to be useful for practically all gene therapy applications. With an NLS-PNA-NA (or an MTS-NLS-PNA-NA), the nucleic acid is delivered to the nucleus of the cell, the nucleic acid is viable for gene expression, the PNA can be used to regulate expression of the nucleic acid, and the NLS maintains the nuclear localization of the nucleic acid. The nucleic acid sequences may encode peptides, polypeptides and/or proteins. Methods exist in the prior art for delivery of nucleic acids to the cytoplasmic membrane of nearly every cell type and tissue and for transport of the nucleic acids across the cytoplasmic membrane; however, efficient transfer of a viable nucleic acid into the nuclear compartment of the cell was a major obstacle to the implementation of gene therapy. Transport of a viable nucleic acid into the nuclear compartment is solved by this invention. The PNA can be synthesized to bind to essentially any known nucleic acid, so gene therapy can be performed with essentially any nucleic acid.

Several examples of genes useful for gene therapy include, but are not limited to: cox 1 (PGH synthase), TGFO (several isoforms), vascular endothelial growth factor (VEGF) (see U.S. Pat. No. 5,869,037 to Crystal et al., incorporated herein by reference), p53 tumor suppressor (see U.S. Pat. No. 5,532,220 to Lee et al., incorporated herein by reference), p94Rb tumor suppressor (see U.S. Pat. No. 5,912,236 to Xu et al., incorporated herein by reference), and the Bax cell death regulator (see U.S. Pat. No. 5,942,490 to Korsmeyer, incorporated herein by reference). One with skill in the art is able to select an appropriate gene for treatment of a disease condition, prepare the gene in an expression vector suitable to the target cell or tissue, and utilize the compositions and methods of the present invention to deliver the gene into the nucleus of the target cells for expression. In other embodiments, the present invention is used to transfect and express genes in cultured cells or bioreactors for the production of peptides and proteins in quantity.

Another example would be the simultaneous application of multiple aspects of the present invention. Therapy involving an NLS-PNA directed toward the coding strand of a mutant p53 allele, at the mutated site, can be combined with an NLS-PNA PNA directed to the non-coding strand of a wild-type p53 allele in a heterozygous (p53 +/−) individual. The result will be the suppression of the mutant (possibly dominant negative) allele and stimulation of expression of the wild-type allele. In null homozygous patients, the mutant alleles can be suppressed with positive therapy utilizing a wild-type gene.

In another example of a nucleic acid sequence for gene therapy would encode alpha-1 antitrypsin (AAT). AAT, the major antiprotease in the lungs, is normally synthesized by the liver and transported to the lungs though the circulation. Because of its molecular size, extracellular AAT cannot access microenvironments or intracellular compartments in the lungs. Therefore, the site of most of AAT's beneficial actions is the extracellular space. During an acute lung insult, proteolytic events critical to the pathogenesis of the lung disease occur both intra- and extracellularly. Most of the direct proteolytic injury in the lung appears to result from release of elastase from activated neutrophils and AAT is the major antiprotease responsible for inactivating this excess elastase. Proteolysis may also be involved in initiation and propagation of lung inflammation. For example, proteolytic mechanisms appear important in inducing neutrophil migration, generating neutrophil chemoattractants, and up-regulating tumor necrosis factor release. Proteolysis may also be involved in the activation of nuclear factor κB (NF-κB), an intracellular transcription factor critical to the induction of genes encoding several cytokines. Intracellular antiproteases can prevent activation and nuclear translocation of NF-κB.

Approximately 150,000 Americans per year develop ARDS, the clinical consequence of acute lung injury. Early and profound activation of the inflammatory cascade is critical in the pathogenesis of ARDS. Mortality may have decreased in recent years, but it remains in the range of 50% in patients with the full blown syndrome. Increased understanding of the pathogenesis of lung injury has resulted in several candidate therapies, some of which are undergoing clinical trials, but to date, no pharmacological intervention has been proven to alter mortality.

Gene, rather than protein, therapy might be more efficacious in ARDS since the gene product would be secreted into the extracellular space inhibiting directly proteolytic injury but also could access the intracellular compartments where many of the detrimental proteolytic events occur.

A nuclear targeted peptide nucleic acid oligomer, or related composition described herein, is useful for the treatment of genetic based disease or disease that can be treated genetically including heart disease, cancer, cerebrovascular diseases, chronic obstructive pulmonary diseases, diabetes, liver diseases including cirrhosis, human immunodeficiency virus, pneumonia, influenza, and nephritis. This is because the PNA portion of an NLS-PNA, an NLS-PNA-NA, an MTS-NLS-PNA, and an MTS-NLS-PNA-NA can be directed toward any genetic element, the compositions can be localized in the nucleus where most genetic reactions take place, annealing of the PNA to a complementary nucleic acid sequence controls expression of the surrounding nucleic acid sequences and regions, and the compositions can be used to introduce any exogenous nucleic acid into a eukaryotic cell, even eukaryotic cell types that have an intact nuclear membrane.

Thus, although there have been described particular embodiments of the present invention of a new and useful Nuclear Targeted Peptide Nucleic Acid, it is not intended that such references be construed as limitations upon the scope of this invention except as set forth in the following claims.

EXAMPLE 1

CONSTRUCTION OF A NUCLEAR LOCALIZATION SEQUENCE-PEPTIDE NUCLEIC ACID (NLS-PNA) AND AN NLS-PNA ANNEALED TO A NUCLEIC ACID (NLS-PNA-NA)

A composition comprising an NLS and a PNA was constructed as follows. A twelve amino acid NLS linked by a peptide bond to an eight base peptide nucleic acid (NLS-PNA) was purchased commercially from Research Genetics, 2130 Memorial Parkway SW, Huntsville, Ala., 35801, USA. The amino acid sequence of the NLS portion was PEVKKKRKPEYP (SEQ ID NO:4). The peptide nucleic acid sequence of the PNA portion was TGGGCAGT. The model/catalogue number was "Custom" as the NLS-PNA was a custom production. The NLS-PNA was produced by solid phase synthesis. The NLS portion of the NLS-PNA comprised a consensus sequence mono-partite NLS designed by the inventor. The PNA portion of the NLS-PNA, also designed by the inventor, targeted an eight base segment of the cytomegalovirus (CMV) promoter. The targeted eight base segment of the CMV promoter comprised the nucleic acid sequence ACTGCCCA.

A control peptide linked to a PNA (referred to herein as control-PNA) was also purchased from the same commercial source for use as an experimental control. The amino acid sequence of the control portion of the control-PNA was PEYRYKYRPEYP (SEQ ID NO:6). The peptide nucleic acid sequence of the PNA portion of the control-PNA remained TGGGCAGT. The control was designed as a scrambled sequence of the NLS given in SEQ ID NO:4 with similar charge and length, but with four tyrosine residues included to facilitate iodination for later experiments.

Annealing of the NLS-PNA to a nucleic acid was performed as follows. The plasmid DNA pCMV-Luc was selected to be the nucleic acid for this experiment. Use of the pCMV-Luc plasmid is only a representative embodiment of the present invention. The pCMV-Luc plasmid comprised a double-stranded DNA that included the luciferase reporter gene under the control of the CMV promoter. The CMV promoter of pCMV-LUC included the target sequence ACTGCCCA for which the present PNA was designed. The NLS-PNA was annealed to the plasmid DNA according to the following protocol. A three molar excess of the NLS-PNA was incubated with the pCMV-Luc plasmid DNA in T10E1 at 50° C. in a thermocycler for 1 hr to promote access of the PNA to the binding region in the double-stranded plasmid. The sample was cooled in steps of 5° C. for 10 minutes at each step until the sample was at 20° C. The gradual cooling promoted annealing of the PNA to the binding region on the plasmid DNA. The product was then stored at 4° C. until needed. Similar methods were used to anneal control-PNA to pCMV-Luc except that the incubation was carried out with a ten molar excess of $^{125}$I labeled control-PNA to pCMV-Luc plasmid DNA.

Next, it was demonstrated that the PNA annealed to the pCMV-Luc plasmid. This was done by comparing the agarose gel mobility of supercoiled plasmid to NLS-PNA-supercoiled DNA. A 1% agarose gel electrophoresis was performed with the following samples. Lane 1 contained Life Technologies 1 KB markers for size determination, lane 2 was blank, lane 3 contained the plasmid alone, lane 4 contained the test of PNA annealing to the plasmid from above. It was noted that the mobility of the plasmid/NLS-PNA in lane 4 was less than that of the parental plasmid in lane 3. Thus, the NLS-PNA was annealed to the plasmid and slowed the migration of the plasmid in the agarose electrophoresis.

Another 1% agarose gel electrophoresis was performed with the following samples. Lane 1 contained Life Technologies 1 KB markers for size determination, lane 2 was blank, lane 3 contained the pCMV-Luc plasmid alone, lane 4 contained $^{125}$I labeled control-PNA annealed to the plasmid, lane 5 contained $^{125}$I labeled control-PNA alone (without plasmid). The gel was dried and an autoradiograph was made. It was noted that a portion of the $^{125}$I labeled control-PNA migrated with the pCMV-Luc plasmid in lane 4. Thus, the control-PNA was annealed to the plasmid using the annealing reaction conditions above.

EXAMPLE 2

METHOD TO DETERMINE PNA DOSE RESPONSE

The prior art suggests that PNAs anneal to double-stranded DNA by displacing one strand and then 2 PNAs form a triplex structure with the complementary region on the target strand. Thus, a 1:2 M/M ratio of double-stranded DNA to PNA would be the least amount of PNA required to bind all targets with 2 PNA molecules (assuming one target per DNA). It is expected that there is a PNA dose response in which varying the amount of PNA in the annealing reaction affects the expression of the annealed reporter gene following transfection. (In this embodiment, excess PNA was not removed from the annealing reaction prior to transfection. One with skill in the art can readily remove the unbound PNA by, for example, membrane retention centrifugation or size exclusion chromatography.)

Therefore, experiments were conducted to determine the affect of, and optimal conditions for, the DNA to PNA (M/M) annealing ratio on the expression of a luciferase reporter gene encoded by the DNA following transfection into sub-confluent HeLa cells. The DNA selected was the pCMV-Luc plasmid which contains a CMV promoter that drives expression of the luciferase reporter gene. This allows for convenient measurements of expression by a luminescence assay (Promega Luciferase Assay, used according to manufacture's instructions). The peptide portion of the control-PNA was twelve residues long and comprised a scrambled peptide of the same charge and length as the NLS portion of the NLS-PNA used in certain embodiments herein (a consensus mono-partite NLS (PEVKKKRKPEYP) (SEQ ID NO:4)). However, the control peptide had four tyrosine residues added for $^{125}$I labeling for use in other studies. The amino acid sequence of the control peptide was PEYRYKYRPEYP (SEQ ID NO:6). The peptide nucleic acid sequence of the PNA was TGGGCAGT and the targeted segment of the CMV promoter was the nucleic acid sequence ACTGCCCA.

The dose response of the DNA:PNA annealing ratio was determined at ratios of 1:3, 1:10, and 1:30 (M/M PNA:DNA) (FIG. 1). The amount of DNA (pCMV-Luc plasmid) was kept constant at 300 ng in the annealing reaction and the amount of control-PNA was altered accordingly. Sub-confluent HeLa cells were transfected because they were known to be easily transfected with a standard DOTMA:DOPE protocol (Lipofectamine(by Gibco-BRL).

The HeLa cells were plated at $4.4 \times 10^5$ cells/1 cm$^2$ and allowed to attach for 24 hr in DMEM plus 10% calf serum and humidified 5% carbon dioxide. The cells were then transfected with annealing reactions (1:3, 1:10, and 1:30 M/M control-PNA to plasmid DNA) using DOTMA:DOPE according to the manufacture's directions in replicate companion wells. After 12 hours incubation in OptiM media with a humidified 5% carbon dioxide atmosphere, the cells were assayed for expression of the luciferase reporter gene using the Promega Luciferase Assay, according to the manufacture's instructions.

Luciferase activity (in relative light units, or RLU) was dependent on the DNA:PNA ratio from the annealing reaction. The data in FIG. 1 demonstrate that the annealing of the control-PNA to the pCMV-Luc plasmid was efficient as a DNA:PNA ratio of 1 to 3 produced significant luciferase expression. It was found that increasing the amount of PNA in the annealing reaction and resulting transfer of the unbound PNA into the transfection reaction, reduced luciferase gene expression. It is contemplated that excess PNA inhibits the transfection reaction or expression of the transfected DNA. Therefore, it is preferred that a DNA to PNA ratio of 1:3 is utilized in the annealing reaction. One with skill in the art can readily determine optimum DNA to PNA ratios for the PNA and DNA system of choice. Furthermore, because annealing of a PNA to the non-coding strand of a nucleic acid stimulates gene expression, it is contemplated that significant gene expression will be observed when using DNA to PNA ratios larger than 1:3, including larger than 1:2, larger than 1:1, and larger than 3:1. This means that the total amount of PNA necessary for efficient transfection and expression is quite low which may be a benefit to the use of PNAs in science and medicine.

EXAMPLE 3

METHOD TO DETERMINE DNA DOSE RESPONSE

The dose response for luciferase expression was determined for varying amounts of pCMV-Luc plasmid DNA, NLS-PNA-pCMV-Luc, and control-PNA-pCMV-Luc transfected into sub-confluent HeLa cells. The NLS-PNA and control-PNA were annealed to pCMV-Luc at a 1:3 M/M ratio of DNA to PNA as described in Examples 1 and 2. The peptide portion of the NLS-PNA was twelve residues long and comprised a consensus mono-partite NLS (PEVKKKRKPEYP) (SEQ ID NO:4). The peptide nucleic acid sequence of the PNA was TGGGCAGT and the targeted segment of the CMV promoter was the nucleic acid sequence ACTGCCCA. Transfections were performed with 300 ng (standard in manufacture's protocol), 100 ng, and 30 ng of plasmid DNA (alone or annealed to the NLS-PNA or the control-PNA) as described above.

Sub-confluent HeLa cells were transfected because they were known to be easily transfected by a standard DOTMA:DOPE protocol. The HeLa cells were plated at $4.4 \times 10^5$ cells/1 $cm^2$ and allowed to attach for 24 hr in DMEM plus 10% calf serum and humidified 5% carbon dioxide. The cells were then transfected with the samples described above according to the manufacture's directions in replicate companion wells. After 12 hours incubation in OptiM media with a humidified 5% carbon dioxide atmosphere, the cells were assayed for expression of the luciferase reporter gene using the Promega Luciferase Assay, according to the manufacture's instructions.

Figure 2:
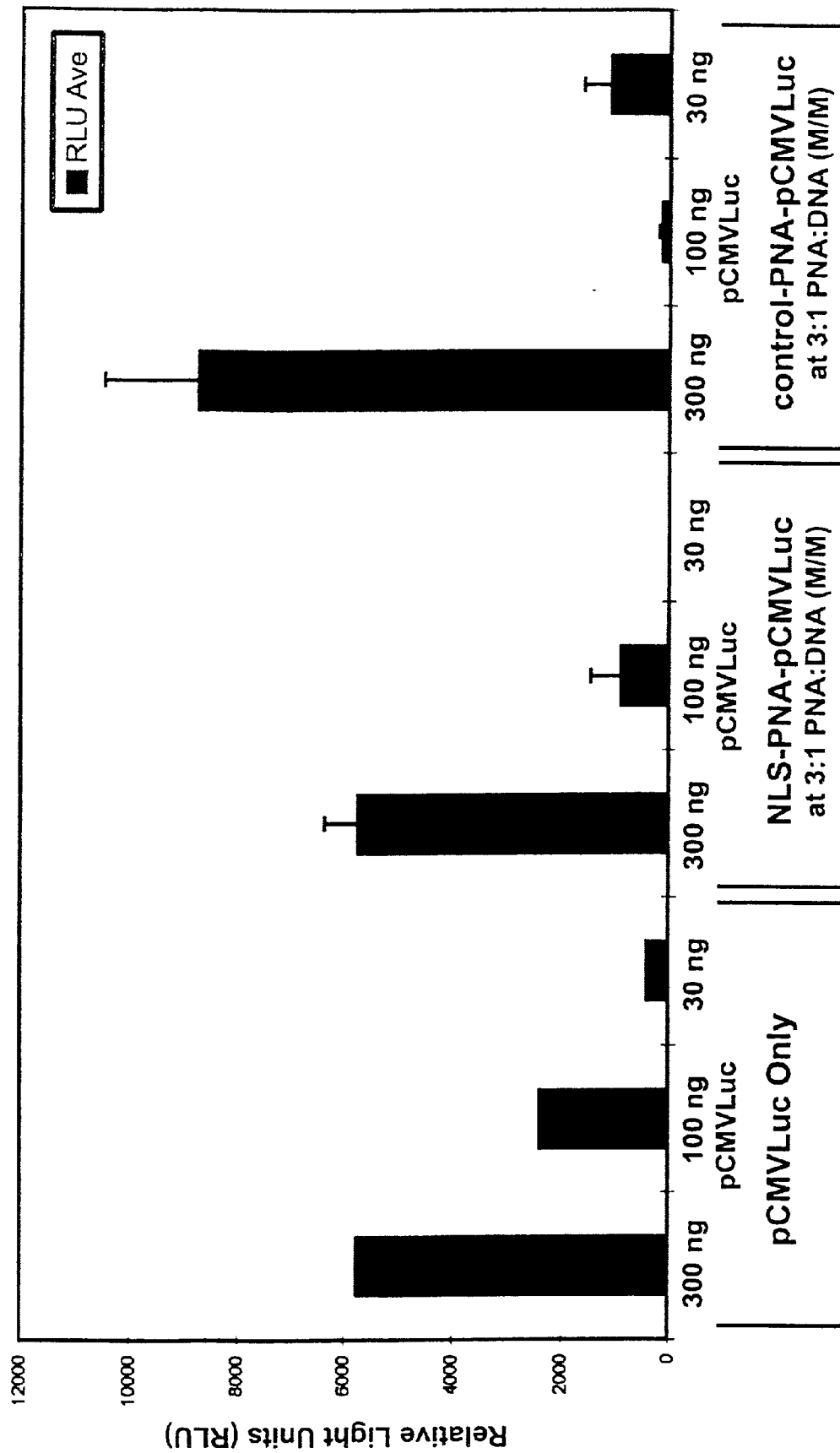
FIG. 2 is a graph showing the relative expression of a luciferase reporter gene (in relative light units) for transfections of sub-confluent HeLa cells with 300 ng, 100 ng, and 30 ng of one of the following: pCMV-Luc (alone), NLS-PNA-pCMVLuc, and control-PNA-pCMVLuc as described in Example 3. This provides a DNA dose response curve.

Luciferase activity (in relative light units, or RLU) was dependent on the amount of DNA used in the transfection at a constant PNA:DNA ratio of 1:3 (FIG. 2). Analysis of the data in FIG. 1 and FIG. 2 show that, as tested, the optimum amount of DNA and the optimum DNA to PNA ratio is 300 ng of plasmid DNA at a 1:3 M/M DNA to PNA. Additional amounts and DNA to PNA ratios can be readily determined by one with skill in the art.

EXAMPLE 4

ANNEALING OF A PNA TO THE NON-CODING STRAND OF THE CMV PROMOTER STIMULATES TRANSCRIPTION

Targeting of a PNA to the non-coding strand in the region of a promoter has been demonstrated to stimulate expression driven by the targeted promoter while targeting of a PNA to the coding strand has been demonstrated to inhibit expression (N. E. Mollegaard (1994) Proc. Natl. Acad. Sci. 91(9) 3892–3895; Good and Nielsen (1997),supra). Therefore, experiments were conducted to demonstrate the ability of an NLS-PNA-NA to transfect a cell and to confirm that annealing of an NLS-PNA to the non-coding strand of the a promoter would stimulate gene expression. In this example, the nucleic acid selected was the pCMV-Luc reporter plasmid. The peptide portion of the NLS-PNA was twelve residues long and comprised a consensus mono-partite NLS (PEVKKKRKPEYP) (SEQ ID NO:4). The peptide portion of the control-PNA was also twelve residues long and comprised a scrambled peptide of the same charge and length as the peptide portion of the NLS-PNA, but with four tyrosine residues added for $^{125}I$ labeling for use in other studies (PEYRYKYRPEYP) (SEQ ID NO:6). The sequence of the PNA was identical in both the NLS-PNA and the control-PNA. The sequence of the PNA was TGGGCAGT and the targeted segment of the CMV promoter was the nucleic acid sequence ACTGCCCA.

HeLa cells, which are known to be easy to transfect at sub-confluent culture conditions, were selected to evaluate whether annealing of the PNA to the non-coding strand of the CMV promoter would increase expression of the luciferase gene in pCMV-Luc. To accomplish this HeLa cells were plated at $4.4 \times 10^5$ cells/1 $cm^2$ and allowed to attach for 24 hr. The cells were then transfected with equal amounts of plasmid DNA. Plasmid-liposome methodology (DOTMA:DOPE) was used to deliver either pCMV-Luc, NLS-PNA-pCMVLuc, or control-PNA-pCMVLuc in replicate companion wells. The ratio of PNA to DNA was 3:1 in the samples containing a PNA annealed to the plasmid. Certain samples of transfected cells were incubated for 6 hours and 12 hours in OptiM media. Other cell samples were incubated for an initial 12 hours in OptiM, then in DMEM plus 10% calf serum for total incubations of 24, 48, 96, and 144 hours post transfection. All incubations were carried out in 5% carbon dioxide under humidified conditions. Upon completion of each incubation, luciferase expression was assayed using the Promega Luciferase Assay, according to the manufacture's directions.

Figure 3:
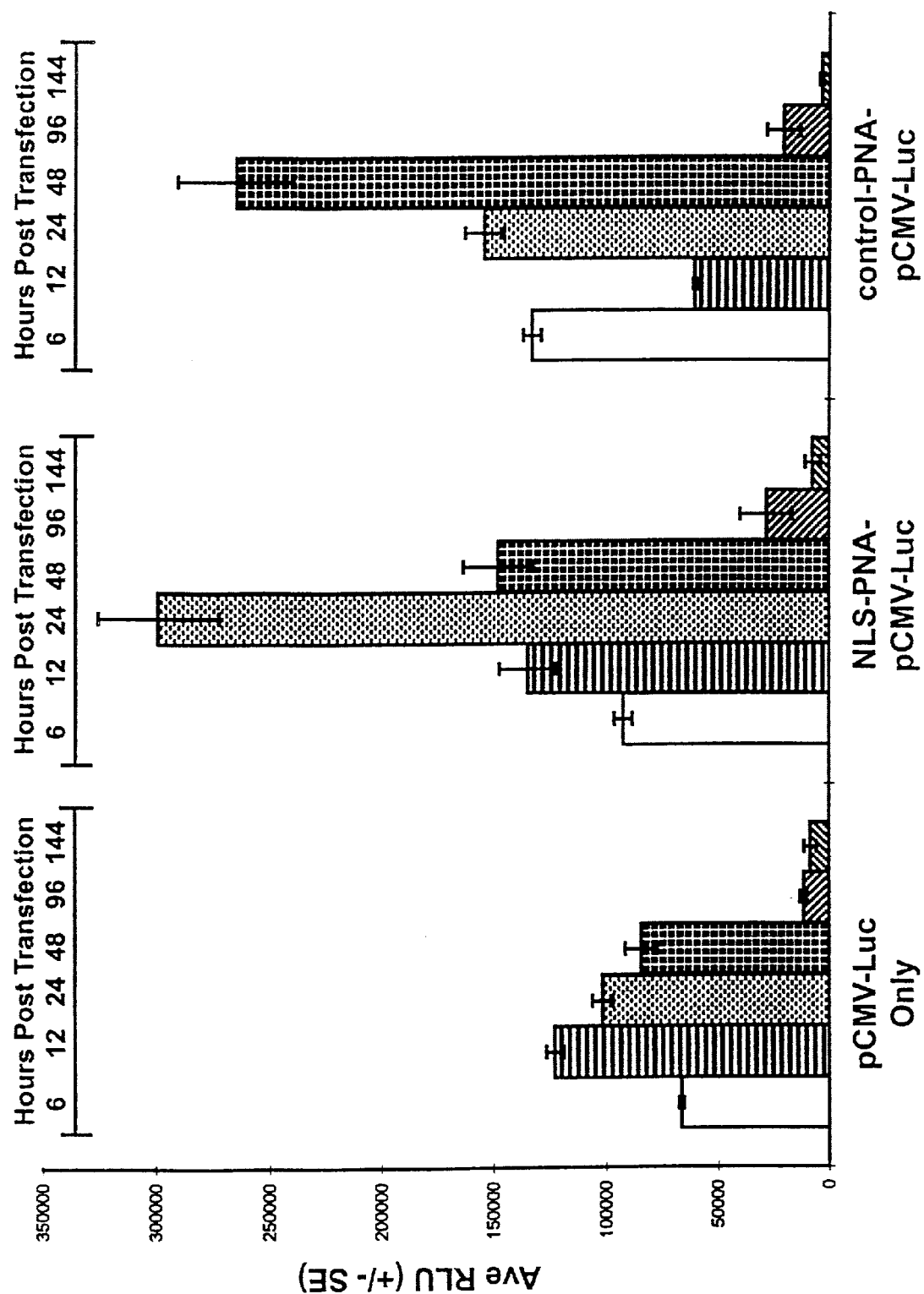
FIG. 3 is a graph showing the relative expression of a luciferase reporter gene (in relative light units) for transfections of sub-confluent HeLa cells with 300 ng of pCMV-Luc plasmid DNA annealed to one of the following: nothing, an NLS-PNA, and a control-PNA; wherein the DNA to PNA ratio was 1:3 in the annealing reaction as described in Example 4. Cells were harvested at 6, 12, 24, 48, 96, and 144 hours after transfection.

FIG. 3 demonstrates the findings of these studies. Annealing of either the NLS-PNA or the control-PNA to the non-coding strand of CMV promoter yielded about two-fold stronger maximum expression compared to pCMV-Luc alone when transfecting sub-confluent HeLa cells. The NLS-PNA samples attained maximum expression at 24 hr as did the pCMV-Luc plasmid alone, while control-PNA samples reached maximum expression at 48 hr. All cells lost expression rapidly after 48 hr, falling to about 10% of maximum expression at 96 hr and 1% to 3% of maximum by 144 hr. Both of the PNA containing reagents appeared to enhance expression from the CMV promoter as predicted. This information indicates that annealing between the PNA and DNA was occurring and that this annealing was tight enough to be maintained through transfection.

EXAMPLE 5

ENHANCED TRANSFECTION IN CONTACT INHIBITED HELA CELLS USING AN NLS-PNA

The transfection of nucleic acids into nucleated eukaryotic cells has been largely ineffectual. In the present invention, nucleic acids can be transfected, localized, and expressed in nucleated cells, among other transfection refractory cell types. Experiments were conducted to demonstrate the ability of an NLS-PNA-NA to transfect a transfection refractory cell type and to confirm the transfection by showing enhanced expression of a reporter gene. Contact inhibited (essentially non-proliferating) HeLa cells were selected as the transfection refractory cell type in this example as these cells have proven to be resistant to transfection. The nucleic acid selected was the pCMV-Luc reporter plasmid.

The pCMV-Luc plasmid was annealed to either NLS-PNA or control-PNA at a DNA to PNA ratio of 1:3 as described herein. The peptide portion of the NLS-PNA was twelve residues long and comprised a consensus monopartite NLS (PEVKKKRKPEYP) (SEQ ID NO:4). The peptide portion of the control-PNA was also twelve residues long and comprised a scrambled peptide of the same charge and length as the peptide portion of the NLS-PNA, but with four tyrosine residues added for $^{251}$I labeling for use in other studies (PEYRYKYRPEYP) (SEQ ID NO:6). The sequence of the PNA was identical in both the NLS-PNA and the control-PNA. The sequence of the PNA was TGGGCAGT and the targeted segment of the CMV promoter was the nucleic acid sequence ACTGCCCA.

The HeLa cells were plated at $4.4 \times 10^5$ cells/1 cm$^2$ and allowed to grow to confluence. The cells were then transfected with equal amounts of plasmid DNA (300 ng) annealed to either NLS-PNA or control-PNA. Plasmid-liposome methodology (DOTMA:DOPE) was used to deliver the agents in replicate companion wells. Samples of transfected cells were incubated for 4 hours, 5, hours and 6 hours post transfection in OptiM. Certain samples of transfected cells were incubated for 6 hours and 12 hours in OptiM media. Other cell samples were incubated for the first 12 hours in OptiM, then in DMEM plus 10% calf serum for total incubations of 24, 48, 96, and 144 hours post transfection. All incubations were carried out in 5% carbon dioxide under humidified conditions. Upon completion of each incubation, luciferase expression was assayed using the Promega Luciferase Assay, according to the manufacture's directions.

FIG. 4 shows the results of these experiments. Transfection of the contact inhibited HeLa cells with NLS-PNA-pCMVLuc resulted in significant luciferase expression within five hours and an additional five-fold increase at six hours. Transfection with control-PNA-pCMVLuc, wherein the sequence of the NLS was scrambled, resulted in essentially no expression of the luciferase reporter gene at any time point tested. Thus, the NLS-PNA was able to transfer the annealed nucleic acid into the nuclear compartment of the nucleated HeLa cells (contact inhibited) wherein the nucleic acid was viable for gene expression. However, a composition comprising a non-NLS-PNA was ineffectual.

Thus, although there have been described particular embodiments of the present invention of a new and useful Nuclear Targeted Peptide Nucleic Acid, it is not intended that such references be construed as limitations upon the scope of this invention except as set forth in the following claims.

What is claimed is:

1. A method of increasing an expression of a wild-type nucleic acid and inhibiting a transcription of a mutant nucleic acid having a mutation in a eukaryotic cell, comprising:
   (a) transfecting the cell with a first composition including a first PNA amino acid chimera having a nuclear localization sequence and a first segment of peptide nucleic acid residues that are complementary to a first binding site on a non-coding strand of the wild-type nucleic acid; and
   (b) transfecting the cell with a second composition including a second PNA amino acid chimera having the nuclear localization sequence and a second segment of peptide nucleic acid residues that are complementary to a second binding site on a coding strand of the mutant nucleic acid and wherein the second binding site includes the mutation; and
   (c) allowing the first composition to anneal to the non-coding strand of the wild-type nucleic acid and the second composition to anneal to the coding strand of the mutant nucleic acid having the mutation, thereby increasing the expression of the wild-type nucleic acid and inhibiting the transcription of the mutant nucleic acid.

2. The method of claim 1, wherein the wild-type nucleic acid is a wild-type p53 nucleic acid and wherein the mutant nucleic acid is a mutant p53 nucleic acid.

3. The method of claim 1, wherein the wild-type nucleic acid and the mutant nucleic acid are endogenous to the eukaryotic cell and wherein the first composition and the second composition are essentially free of a nucleic acid molecule prior to the transfecting step.

4. The method of claim 1, wherein the first composition and the second composition further include a membrane transport sequence.

5. A method of increasing an expression of a first nucleic acid and inhibiting a transcription of a second nucleic acid in a eukaryotic cell, comprising:
   (a) transfecting the cell with a first composition including a first PNA amino acid chimera having a nuclear localization sequence and a first segment of peptide nucleic acid residues that are complementary to a first binding site on a non-coding strand of the first nucleic acid; and
   (b) transfecting the cell with a second composition including a second PNA amino acid chimera having the nuclear localization sequence and a second segment of peptide nucleic acid residues that are complementary to a second binding site on a coding strand of the second nucleic acid; and
   (c) allowing the first composition to anneal to the non-coding strand of the first nucleic acid and the second composition to anneal to the coding strand of the second nucleic acid, thereby increasing the expression of the first nucleic acid and inhibiting the transcription of the second nucleic acid.

6. The method of claim 5 wherein the first composition further includes a first membrane transport sequence and the second composition further includes a second membrane transport sequence.

7. The method of claim 5, wherein the first nucleic acid and the second nucleic acid are endogenous to the eukaryotic cell and wherein the first composition and the second composition are essentially free of a nucleic acid molecule prior to the transfecting step.

8. A composition, comprising:
    (a) a nuclear localization sequence; and
    (b) a peptide nucleic acid oligomer, wherein the nuclear localization sequence and the peptide nucleic acid oligomer are linked by a peptide bond.

9. The composition of claim 8, wherein the peptide nucleic acid oligomer includes at least a first portion that is complementary to an endogenous nucleic acid of an eukaryotic cell.

10. The composition of claim 9, further comprising a membrane transport sequence.

11. A composition, comprising:
    (a) a nuclear localization sequence;
    (b) a peptide nucleic acid oligomer having at least one portion complementary to an endogenous nucleic acid of an eukaryotic cell; and
    (c) a membrane transport sequence, wherein the nuclear localization sequence, the peptide nucleic acid, and the membrane transport sequence are combined in any order.

12. A process of making an antisense nucleic acid, comprising:
    (a) providing amino acids and peptide nucleic acids;
    (b) selecting a target region of an endogenous nucleic acid; and
    (c) combining the amino acids and the peptide nucleic acids in a sequence specific order to form a PNA amino acid chimera including a peptide nucleic acid having at least a portion that is complementary to the target region and a nuclear localization sequence, wherein the peptide nucleic acid and the nuclear localization sequence are linked by a peptide bond.

13. The process of claim 12, wherein the peptide nucleic acid and the nuclear localization sequence are linked by a single peptide bond.

14. The process of claim 12, wherein the PNA amino acid chimera further includes a membrane transport sequence.

15. A process of making an antisense nucleic acid, comprising:
    (a) providing amino acids and peptide nucleic acids;
    (b) selecting a target region of an endogenous nucleic acid; and
    (c) combining the amino acids and the peptide nucleic acids in a sequence specific order to form a PNA amino acid chimera including a peptide nucleic acid having at least a portion that is complementary to the target region, a nuclear localization sequence, and a membrane transport sequence.

\* \* \* \* \*

SEQUENCE LISTING

<160> NUMBER OF SEQ ID NOS: 6

<210> SEQ ID NO 1
<211> LENGTH: 16
<212> TYPE: PRT
<213> ORGANISM: Homo sapiens

<400> SEQUENCE: 1

Ala Ala Val Ala Leu Leu Pro Ala Val Leu Leu Ala Leu Leu Ala Pro
 1               5                  10                  15

<210> SEQ ID NO 2
<211> LENGTH: 25
<212> TYPE: PRT
<213> ORGANISM: Xenopus sp.

<400> SEQUENCE: 2

Leu Val Arg Lys Lys Arg Lys Thr Glu Glu Glu Ser Pro Leu Lys Asp
 1               5                  10                  15

Lys Asp Ala Lys Lys Ser Lys Gln Glu
                20                  25

<210> SEQ ID NO 3
<211> LENGTH: 7
<212> TYPE: PRT
<213> ORGANISM: Simian virus 40

<400> SEQUENCE: 3

Pro Lys Lys Lys Arg Lys Val
 1               5

```
<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: consensus
      NLS peptide

<400> SEQUENCE: 4

Pro Glu Val Lys Lys Lys Arg Lys Pro Glu Tyr Pro
 1               5                  10

<210> SEQ ID NO 5
<211> LENGTH: 29
<212> TYPE: PRT
<213> ORGANISM: Human immunodeficiency virus

<400> SEQUENCE: 5

Cys Phe Ile Thr Lys Ala Leu Gly Ile Ser Tyr Gly Arg Lys Lys Arg
 1               5                  10                  15

Arg Gln Arg Arg Arg Pro Pro Gln Gly Ser Gln Thr His
            20                  25

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: consensus
      NLS peptide

<400> SEQUENCE: 6

Pro Glu Tyr Arg Tyr Lys Tyr Arg Pro Glu Tyr Pro
 1               5                  10
```